(12) United States Patent
Lee et al.

(10) Patent No.: US 9,861,574 B2
(45) Date of Patent: Jan. 9, 2018

(54) 2-FLUORO-MODIFIED RNAS AS IMMUNOSTIMULATORS

(71) Applicant: DUKE UNIVERSITY, Durham, NC (US)

(72) Inventors: Jaewoo Lee, Durham, NC (US); Johannes Urban, Durham, NC (US); Bruce A. Sullenger, Durham, NC (US)

(73) Assignee: Duke University, Durham, NC (US)

( * ) Notice: Subject to any disclaimer, the term of this patent is extended or adjusted under 35 U.S.C. 154(b) by 33 days.

(21) Appl. No.: 14/783,717

(22) PCT Filed: Apr. 9, 2014

(86) PCT No.: PCT/US2014/033518
§ 371 (c)(1),
(2) Date: Oct. 9, 2015

(87) PCT Pub. No.: WO2014/169049
PCT Pub. Date: Oct. 16, 2014

(65) Prior Publication Data
US 2016/0030332 A1  Feb. 4, 2016

Related U.S. Application Data

(60) Provisional application No. 61/810,073, filed on Apr. 9, 2013.

(51) Int. Cl.
| | | |
|---|---|---|
| A61K 9/00 | (2006.01) |
| A61K 31/7115 | (2006.01) |
| C12N 15/115 | (2010.01) |
| C12N 15/117 | (2010.01) |
| A61K 9/127 | (2006.01) |
| A61K 39/00 | (2006.01) |

(52) U.S. Cl.
CPC ............ *A61K 9/0012* (2013.01); *A61K 9/127* (2013.01); *A61K 31/7115* (2013.01); *A61K 39/0011* (2013.01); *C12N 15/115* (2013.01); *C12N 15/117* (2013.01); *C12N 2310/16* (2013.01); *C12N 2310/17* (2013.01); *C12N 2310/31* (2013.01); *C12N 2310/33* (2013.01); *C12N 2310/335* (2013.01); *C12N 2310/531* (2013.01); *C12N 2320/31* (2013.01); *C12N 2320/32* (2013.01)

(58) Field of Classification Search
USPC ........... 435/6.1, 91.1, 91.31, 375, 455, 458; 514/44; 536/23.1, 24.5; 424/277.1, 424/278.1, 450
See application file for complete search history.

(56) References Cited

U.S. PATENT DOCUMENTS

| | | | |
|---|---|---|---|
| 2010/0260788 A1 | 10/2010 | Debelak et al. | |
| 2012/0107272 A1* | 5/2012 | Manoharan ............ | C07H 21/00 424/85.4 |
| 2012/0220761 A1 | 8/2012 | Zlatev et al. | |

FOREIGN PATENT DOCUMENTS

| | | | |
|---|---|---|---|
| WO | WO 2014/049079 | * | 3/2014 |
| WO | WO 2014/049079 | | 4/2014 |
| WO | WO 2014/066915 | | 5/2014 |

OTHER PUBLICATIONS

Uzri et al, J. Virol., vol. 83, No. 9, pp. 4174-4184 (2009).*
Abbas, Y.M., Pichlmair, A., Gorna, M.W., Superti-Furga, G. and Nagar, B. (2013) Structural basis for viral 5'-PPP-RNA recognition by human IFIT proteins, Nature, 2013, pp. 60-64, vol. 494.
Besch, R., Poeck, H., Hohenauer, T., Senft, D., Hacker, G., Berking, C., Hornung, V., Endres, S., Ruzicka, T., Rothenfusser, S. et al., Proapoptotic signaling induced by RIG-I and MDA-5 results in type I interferon-independent apoptosis in human melanoma cells, The Journal of clinical investigation, 2009, pp. 2399-2411, vol. 119:8.
Chakravarthy, K.V., Bonoiu, A.C., Davis, W.G., Ranjan, P., Ding, H., Hu, R., Bowzard, J.B., Bergey, E.J., Katz, J.M., Knight, P.R. et al,. Gold nanorod delivery of an ssRNA immune activator inhibits pandemic H1N1 influenza viral replication, Proceedings of the National Academy of Sciences of the United States of America, 2010, pp. 10172-10177, vol. 107:22.
Cheng, Y.S. and Xu, F, Anticancer function of polyinosinic-polycytidylic acid. Cancer biology & therapy, 2011, 1219-1223, vol. 10:12.
Colli, M.L., Nogueira, T.C., Allagnat, F., Cunha, D.A., Gurzov, E.N., Cardozo, A.K., Roivainen, M., Op De Beeck, A. and Eizirik, D.L., Exposure to the viral by-product dsRNA or Coxsackievirus B5 triggers pancreatic beta cell apoptosis via a Bim / Mcl-1 imbalance, PLoS pathogens, 2011, e1002267, vol. 7:9.
Dassie, J.P., Liu, X.Y., Thomas, G.S., Whitaker, R.M., Thiel, K.W., Stockdale, K.R., Meyerholz, D.K., Mcaffrey, A.P., Mcnamara II, J.O., and Giangrande, P.H., Systemic administration of optimized aptamer-siRNA chimeras promotes regression of PSMA-expressing tumors, Nature biotechnology, 2009, pp. 839-849, vol. 27.
Diebold, S.S., Kaisho, T., Hemmi, H., Akira, S., Reis, E Sousa, C., Innate antiviral responses by means of TLR7-mediated recognition of single-stranded RNA, Science, 2004, pp. 1529-1531, vol. 303.

(Continued)

*Primary Examiner* — Jane Zara
(74) *Attorney, Agent, or Firm* — Andrus Intellectual Property Law, LLP

(57) ABSTRACT

Methods of inhibiting the growth of cells or inducing cell death by contacting the cells with or introducing into the cells a composition including a 5' triphosphate, 2' fluoro-modified pyrimidine non-linear single stranded RNA at least 17 nucleotides long with a least 3 base pairings or a 5' triphosphate, 2' fluoro-modified double stranded RNA at least 17 base pairs long in an amount effective to inhibit cell growth, induce cell death or induce cytokine production by the cells. The methods also include administration of the compositions to a subject. The subject may have a proliferative disorder or infectious disease and administration of the compositions provided herein may treat the disorder or disease.

22 Claims, 14 Drawing Sheets

(56) References Cited

OTHER PUBLICATIONS

Estornes, Y., Toscano, F., Virard, F., Jacquemin, G., Pierrot, A., Vanbervliet, B., Bonnin, M., Lalaoui, N., Mercier-Gouy, P., Pacheco, Y. et al, dsRNA induces apoptosis through an atypical death complex associating TLR3 to caspase-8, Cell death and differentiation, 2012, 1482-1494, vol. 19.

Emens, L.A., Chemoimmunotherapy, Cancer J, 2010, pp. 295-303, vol. 16:4.

Gorina, R., Santalucia, T., Petengief, V., Ejarque-Ortiz, A., Saura, J. and Planas, A.M., Astrocytes are very sensitive to develop innate immune responses to lipid-carried short interfering RNA, Glia, 2009, pp. 93-107, vol. 57:1.

Heil, F., Hemmi, H., Hochrein, H., Ampenberger, F., Kirschning, C., et al., Species-specific recognition of single-stranded RNA via toll-like receptor 7 and 8, Science, 2004, pp. 1526-1529, vol. 303.

Hornung, V., Ellegast, J., Kim, S., Brzozka, K., Jung, A., Kato, H., Poeck, H., Akira, S., Conzelmann, K..K.., Schlee, M. et al., 5'-Triphosphate RNA is the ligand for RIG-I, Science, 2006, pp. 994-997, vol. 314.

Hwang, S.Y., Sun, H.Y., Lee, K.H., Oh, B.H., Cha, Y.J., Kim, B.H. and Yoo, J.Y., 5'-Triphosphate-RNA-independent activation of RIG-I via RNA aptamer with enhanced antiviral activity, Nucleic acids research, 2012, pp. 2724-2733, vol. 40:6.

Ishibashi, O., Ali, M.M., Luo, S.S., Ohba, T., Katabuchi, H., Takeshita, T. and Takizawa, T., Short RNA duplexes elicit RIG-I-mediated apoptosis in a cell type- and length-dependent manner, Science signaling, 2011, ra74, vol. 4.

Jiang, M., Osterlund, P., Sarin, L.P., Poranen, M.M., Bamford, D.H., Guo, D. and Julkunen, I., Innate immune responses in human monocyte-derived dendritic cells are highly dependent on the size and the 5' phosphorylation of RNA molecules, J Immunol, 2011, pp. 1713-1721, vol. 187.

Jiang, F., Ramanathan, A., Miller, M.T., Tang, G.Q., Gale, M., Jr., et al., Structural basis of RNA recognition and activation by innate immune receptor RIG-I, Nature, 2011, pp. 423-427, vol. 479.

Jockel, S., Nees, G., Sommer, R., Zhao, Y., Cherkasov, D., Hori, H., Ehm, G., Schnare, M., Nain, M., Kaufmann, A. et al., The 2'-O-methylation status of a single guanosine controls transfer RNA-mediated Toll-like receptor 7 activation or inhibition, The Journal of experimental medicine, 2012, pp. 235-241, vol. 209.

Judge, A.D., Bola, G., Lee, A.C. and Maclachlan, I., Design of noninflammatory synthetic siRNA mediating potent gene silencing in vivo, Molecular therapy : the journal of the American Society of Gene Therapy, 2006, pp. 494-505, vol. 13.

Kubler, K., Gehrke, N., Riemann, S., Bohnert, V., Zillinger, T., Hartmann, E., Polcher, M., Rudlowski, C., Kuhn, W., Hartmann, G. et al., Targeted activation of RNA helicase retinoic acid-inducible gene-I induces proimmunogenic apoptosis of human ovarian cancer cells, Cancer research, 2010, pp. 5293-5304, vol. 70.

Kubler, K., Tho Pesch, C., Gehrke, N., Riemann, S., Dassler, J., Coch, C., Landsberg, J., Wimmenauer, V., Polcher, M., Rudlowski, C. et al., Immunogenic cell death of human ovarian cancer cells induced by cytosolic poly(I:C) leads to myeloid cell maturation and activates NK cells, European journal of immunology, 2011, pp. 3028-3039, vol. 41.

Lehmann, S.M., Rosenberger, K., Kruger, C., Habbel, P., Derkow, K., Kaul D., Rybak, A., Brandt, C., Schott, E., Wulczyn, F.G. et al., Extracellularly delivered single-stranded viral RNA causes neurodegeneration dependent on TLR7, J Immunol, 2012, pp. 1448-1458, vol. 189.

Lion, E., Anguille, S., Berneman, Z.N., Smits, E.L. and Van Tendeloo, V.F., Poly(I:C) enhances the susceptibility of leukemic cells to NK cell cytotoxicity and phagocytosis by DC, PloS one, 2011, e20952, vol. 6.

Longley, D.B., Harkin, D.P. and Johnston, P.G., 5-fluorouracil: mechanisms of action and clinical strategies, Nature review: Cancer, 2003, pp. 330-338, vol. 3:5.

Lotze, M.T., Zeh, H.J., Rubartelli, A., Sparverp, L.J., Amoscato, A.A., Washburn, N.R., Devera, M.E., Liang, X., Tor, M. and Billiar, T., The grateful dead: damage-associated molecular pattern molecules and reduction/oxidation regulate immunity, Immunological reviews, 2007, pp. 60-81, vol. 220.

Manoharan, M., Akinc, A., Pandey, R.K., Qin, J., Hadwiger, P., John, M., Mills, K., Charisse, K., Maier, M.A., Nechev, L. et al., Unique gene-silencing and structural properties of 2'-fluoro-modified siRNAs, Angewandte Chemie, 2011, pp. 2284-2288, vol. 50.

Matsushima-Miyagi, T., Hatano, K., Nomura, M., Li-Wen, L., Nishikawa, T., Saga, K., Shimbo, T. and Kaneda, Y., Trail and Noxa are selectively upregulated in prostate cancer cells downstream of the RIG-I/MAVS signaling pathway by nonreplicating Sendai virus particles, Clinical cancer research : an official journal of the American Association for Cancer Research, 2012, pp. 6271-6283, vol. 18.

Nallagatla, S.R. and Bevilacqua, P.C., Nucleoside modifications modulate activation of the protein kinase PKR in an RNA structure-specific manner, RNA, 2008, pp. 1201-1213, vol. 14.

Ni, X., Zhang, Y., Ribas, J., Chowdhury, W.H., Castanares, M., Zhang, Z., Laiho, M., Deweese, T.L. and Lupold, S.E., Prostate-targeted radiosensitization via aptamer-shRNA chimeras in human tumor xenografts, The Journal of clinical investigation, 2011, pp. 2383-2390, vol. 121.

Nimjee, S.M., Lohrmann, J.D., Wang, H., Snyder, D.J., Cummings, T.J., Becker, R.C., Oney, S. and Sullenger, B.A., Rapidly regulating platelet activity in vivo with an antidote controlled platelet inhibitor, Molecular therapy : the journal of the American Society of Gene Therapy, 2012, pp. 391-397, vol. 20.

Padilla, R. and Sousa, R., A Y639F/H784A T7 RNA polymerase double mutant displays superior properties for synthesizing RNAs with non-canonical NTPs, Nucleic acids research, 2002, e138, vol. 30.

Pallan, P.S., Greene, E.M., Jicman, P.A., Pandey, R.K., Manoharan, M., Rozners, E. and Egli, M., Unexpected origins of the enhanced pairing affinity of 2'-fluoro-modified RNA, Nucleic acids research, 2011, pp. 3482-3495, vol. 39.

Poeck, H., Besch, R., Maihoefer, C., Renn, M., Tormo, D., Morskaya, S.S., Kirschnek, S., Gaffal, E., Landsberg, J., Hellmuth, J. et al., 5'-Triphosphate-siRNA: turning gene silencing and RIG-I activation against melanoma, Nature medicine, 2008, pp. 1256-1263, vol. 14.

Robbins, M., Judge, A., Liang, L., McClintock, K., Yaworski, E. and MacLachlan, I., 2'-O-methyl-modified RNAs act as TLR7 antagonists, Molecular therapy : the journal of the American Society of Gene Therapy, 2007, pp. 1663-1669, vol. 15.

Saito, T., Owen, D.M., Jiang, F., Marcotrigiano, J. and Gale, M., Jr., Innate immunity induced by composition-dependent RIG-I recognition of hepatitis C virus RNA, Nature, 2008, pp. 523-527, vol. 454.

Schmidt, A., Schwerd, T., Hamm, W., Hellmuth, J.C., Cui, S., Wenzel, M., Hoffmann, F.S., Michallet, M.C., Besch, R., Hopfner, K.P. et al., 5'-triphosphate RNA requires base-paired structures to activate antiviral signaling via RIG-I, Proceedings of the National Academy of Sciences of the United States of America, 2009, pp. 12067-12072, vol. 106.

Shir, A., Ogris, M., Wagner, E. and Levitzki, A., EGF receptor-targeted synthetic double-stranded RNA eliminates glioblastoma, breast cancer, and adenocarcinoma tumors in mice, PLoS medicine, 2006, e6, vol. 3.

Sioud, M., Single-stranded small interfering RNA are more immunostimulatory than their double-stranded counterparts: a central role for 2'-hydroxyl uridines in immune responses, European journal of immunology, 2006, pp. 1222-1230, vol. 36.

Sioud, M., Development of TLR7/8 small RNA antagonists, Methods Mol Biol,, 2010, pp. 387-394, vol. 629.

Takahasi, K., Kumeta, H., Tsuduki, N., Narita, R., Shigemoto, T., Hirai, R., Yoneyama, M., Horiuchi, M., Ogura, K., Fujita, T. et al., Solution structures of cytosolic RNA sensor MDA5 and LGP2 C-terminal domains: identification of the RNA recognition loop in RIG-I-like receptors, The Journal of biological chemistry, 2009, pp. 17465-17474, vol. 284.

(56) References Cited

OTHER PUBLICATIONS

Takahasi, K., Yoneyama, M., Nishihori, T., Hirai, R., Kumeta, H., Narita, R., Gale, M., Jr., Inagako, F. and Fujita, T., Nonself RNA-sensing mechanism of RIG-I helicase and activation of antiviral immune responses, Molecular cell, 2008, pp. 428-440, vol. 29.

Thiel, K.W. and Giangrande, P.H., Intracellular delivery of RNA-based therapeutics using aptamers, Therapeutic delivery, 2010, pp. 849-861, vol. 1.

Tormo, D., Checinska, A., Alonso-Curbelo, D., Perez-Guuarro, E., Canon, E., Riveiro-Falkenbach, E., Calvo, T.G., Larribere, L., Megias, D., Mulero, F. et al., Targeted activation of innate immunity for therapeutic induction of autophagy and apoptosis in melanoma cells, Cancer cell, 2009, pp. 103-114, vol. 16.

Toroney, R., Hull, C.M., Sokoloski, J.E., Bevilacqua, P.C., Mechanistic characterization of the 5'-triphosphate-dependent activation of PKR: lack of 5'-end nucleobase specificity, evidence for a distinct triphosphate binding site, and a critical role for the dsRBD, RNA, 2012, pp. 1862-1874, vol. 18.

Trinchieri, G., Type I interferon: friend or foe?, The Journal of experimental medicine, 2010, pp. 2053-2063, vol. 207.

Trinchieri, G. and Sher, A., Cooperation of Toll-like receptor signals in innate immune defense, Nature reviews. Immunology, 2007, pp. 179-190, vol. 7.

Uzri, D. and Gehrke, L., Nucleotide sequences and modifications that determine RIG-I/RNA binding and signaling activities, Journal of virology, 2009, pp. 4174-4184, vol. 83.

Wang, Y., Ludwig, J., Schuberth, C., Goldeck, M., Schlee, M., Li, H., Juranek, S., Sheng, G., Micura, R., Tuschl, T. et al., Structural and functional insights into 5'-ppp RNA pattern recognition by the innate immune receptor RIG-I, Nature structural & molecular biology, 2010, pp. 781-787, vol. 17.

Yoneyama, M. and Fujita, T., RNA recognition and signal transduction by RIG-I-like receptors, Immunological reviews, 2009, pp. 54-65, vol. 227.

Yu, M. and Levine, S.J., Toll-like receptor, RIG-I-like receptors and the NLRP3 inflammasome: key modulators of innate immune responses to double-stranded RNA viruses, Cytokine & growth factor reviews, 2011, pp. 63-72, vol. 22.2.

Yu, N., Zhang, S., Sun, T., Kang, K., Guan, M. and Xiang, L., Double-stranded RNA induces melanocyte death via activation of Toll-like receptor 3, Experimental dermatology, 2011, pp. 134-139, vol. 20.2.

Zust, R., Cervantes-Barragan, L., Habjan, M., Maier, R., Neuman, B.W., Ziebuhr, J., Szretter, K.J., Baker, S.C., Barchet, W., Diamond, M.S. et al, Ribose 2'-O-methylation provides a molecular signature for the distinction of self and non-self mRNA dependent on the RNA sensor Mda5, Nature immunology, 2011, pp. 137-143, vol. 12.2.

\* cited by examiner

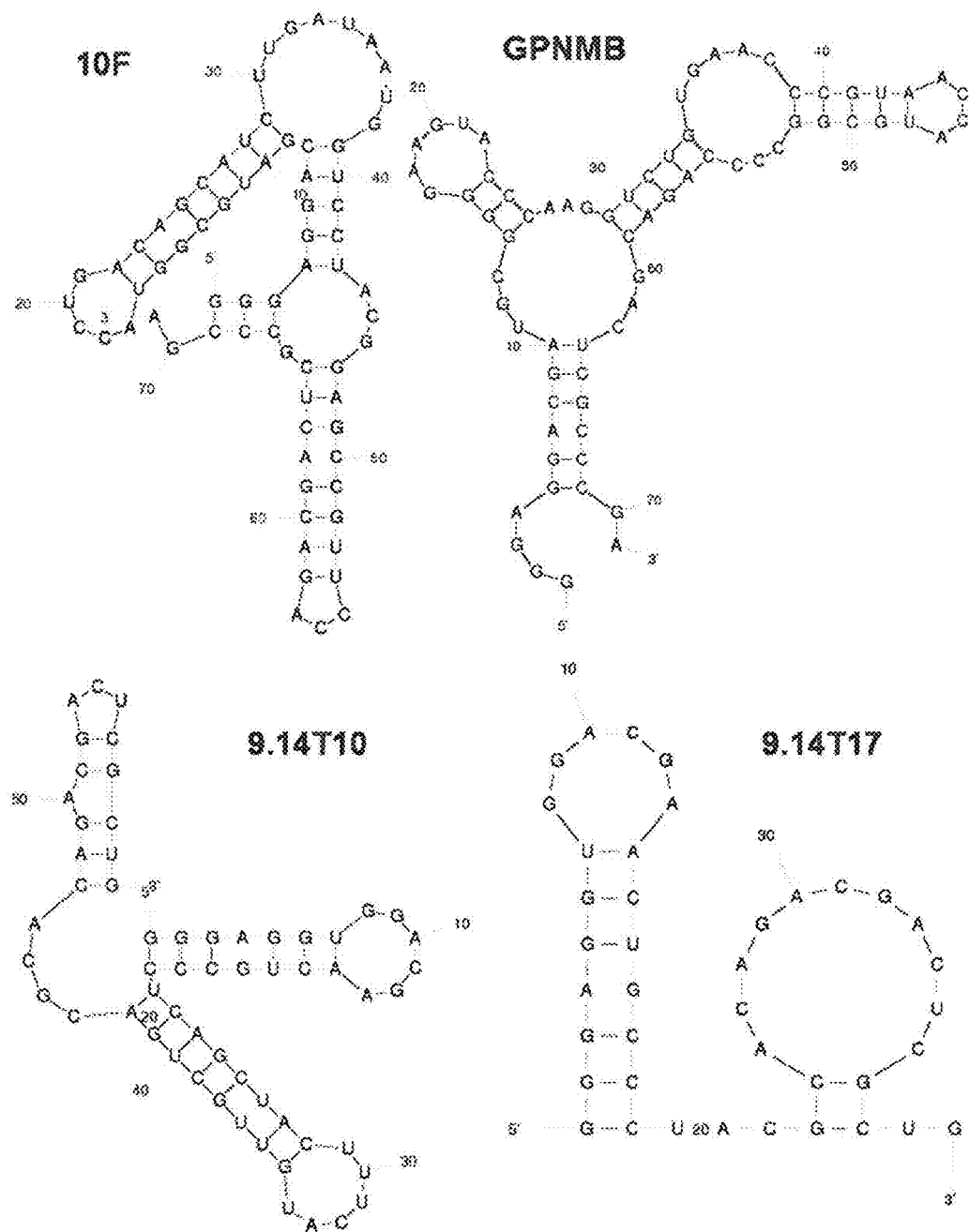

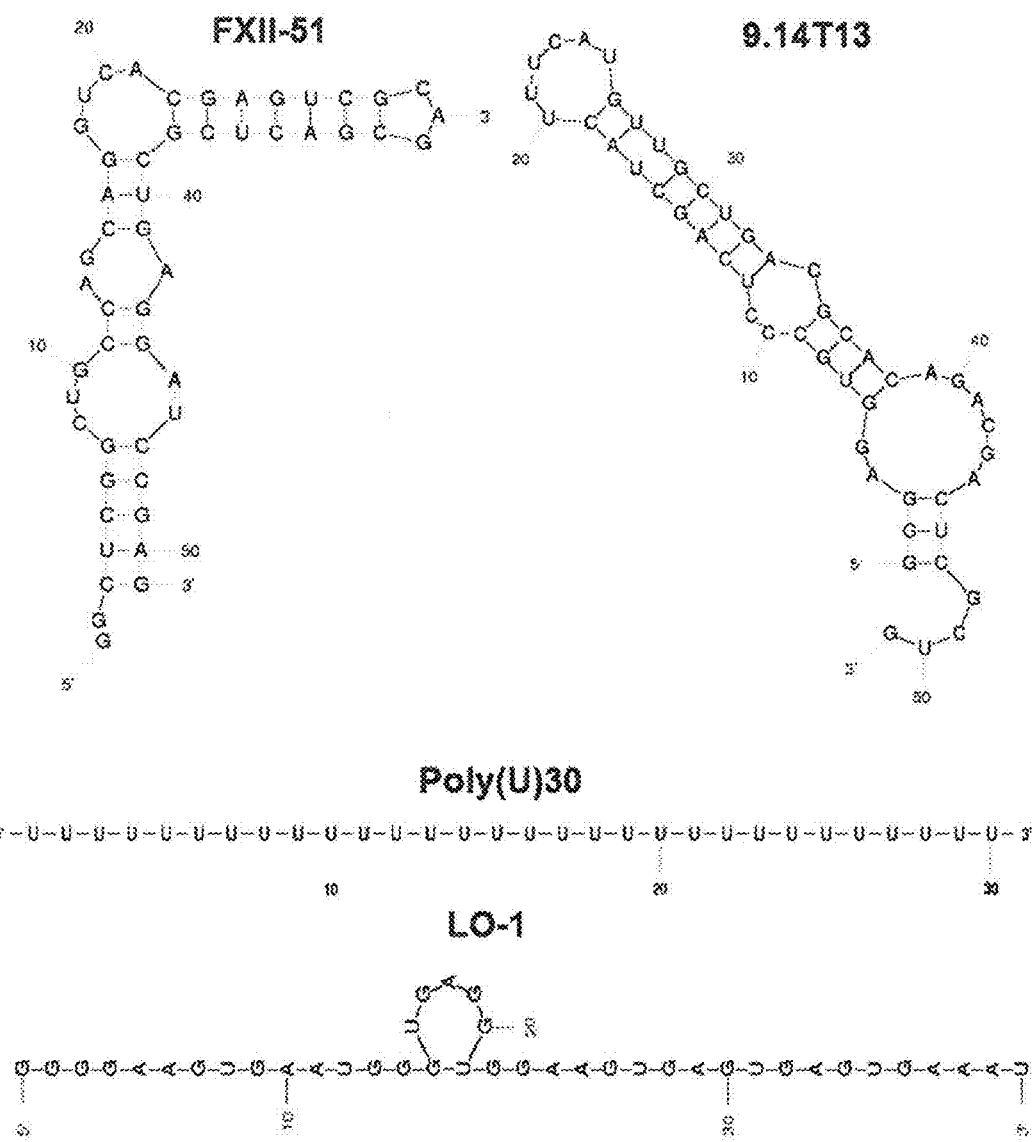
Figure 1A (2) (Continued from Previous Page)

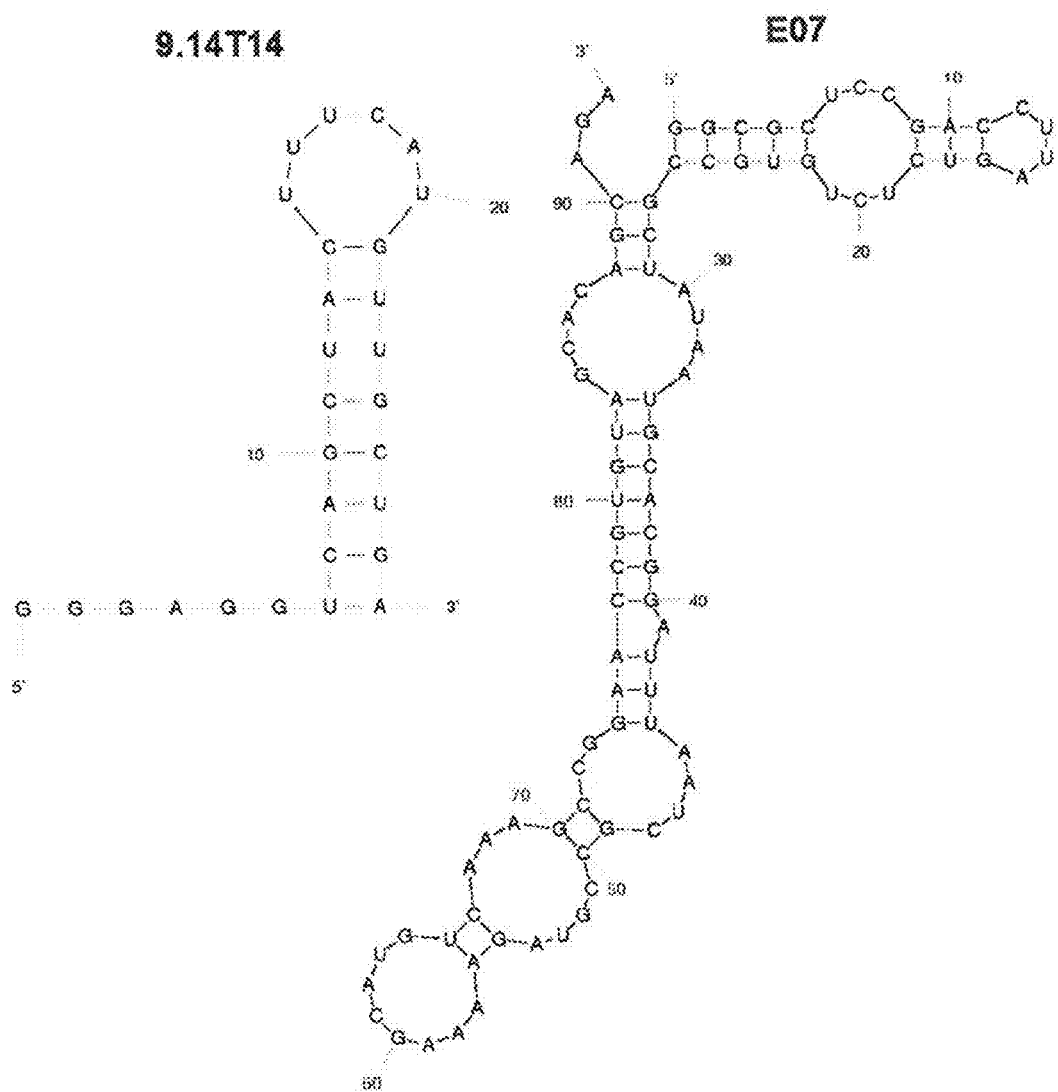
Figure 1A (3)(Continued from Previous Page)

Figure 3
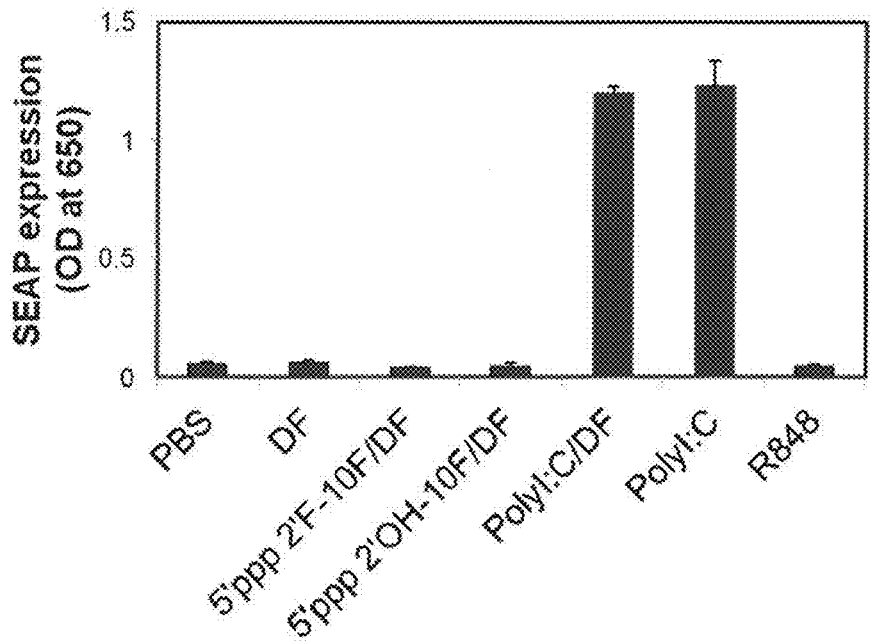
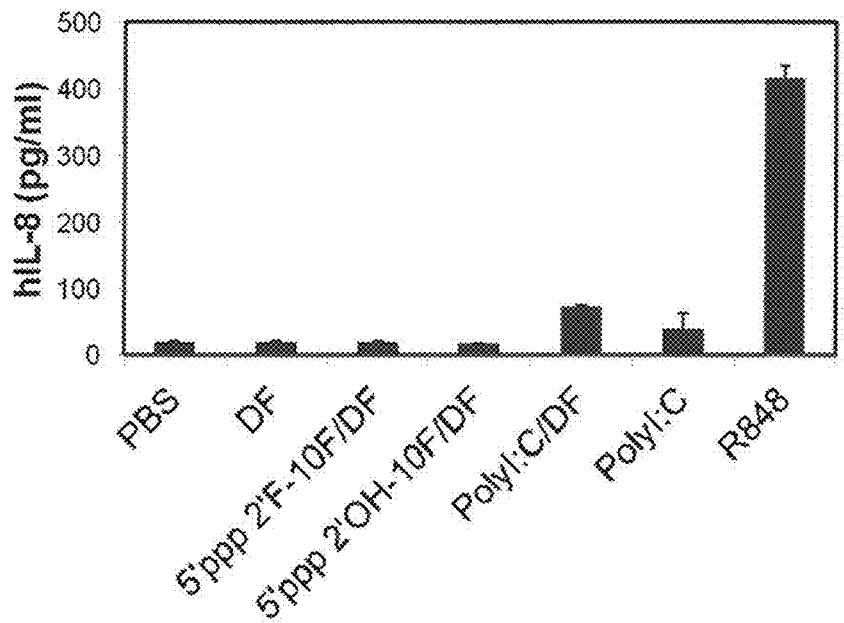

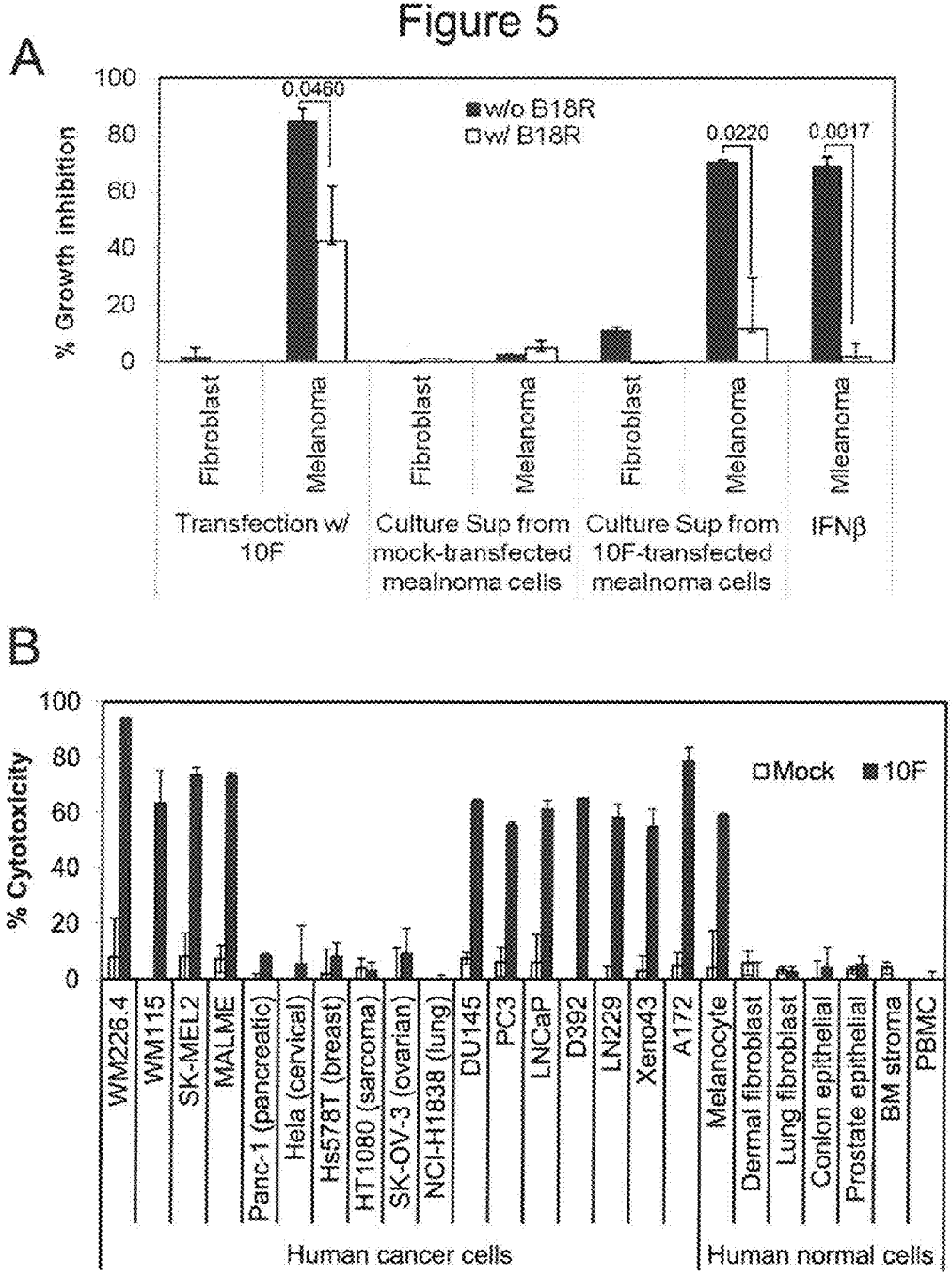

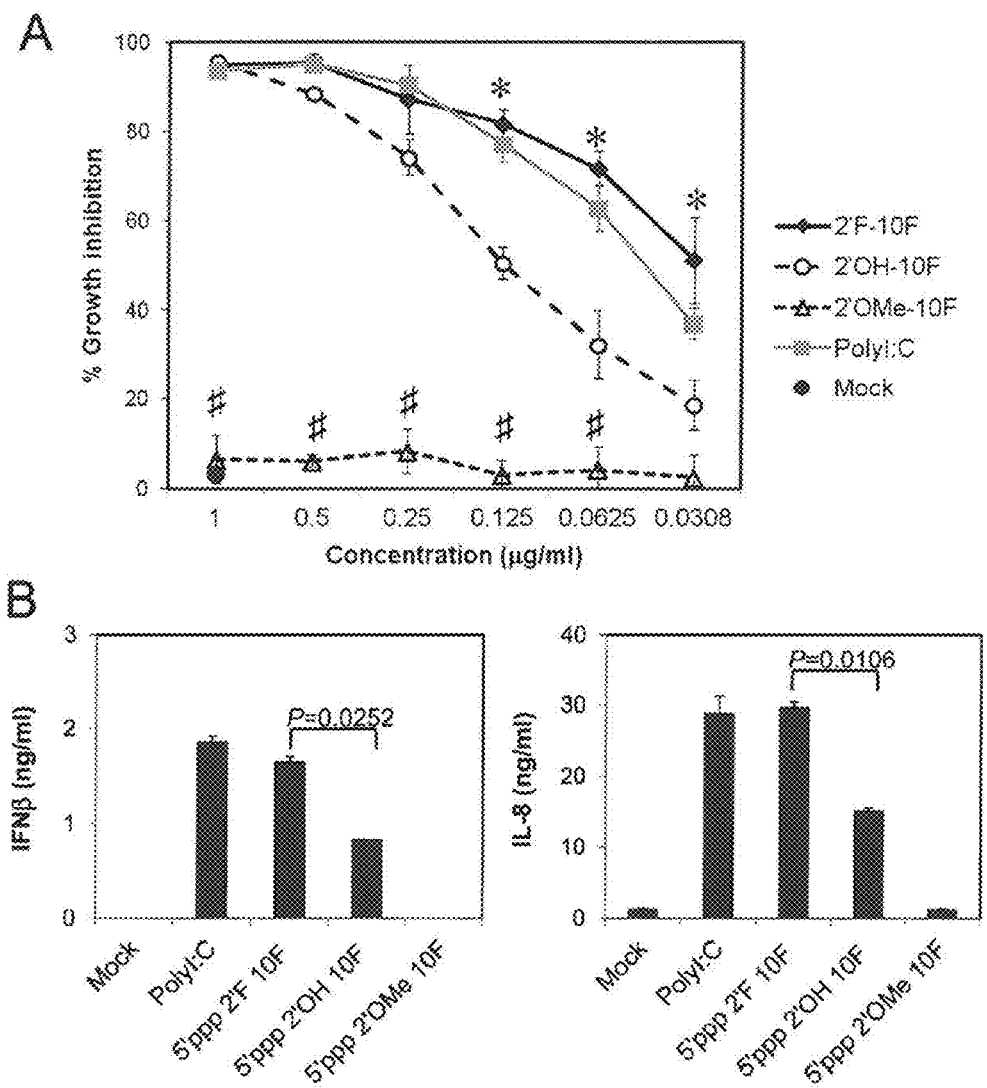

Figure 6
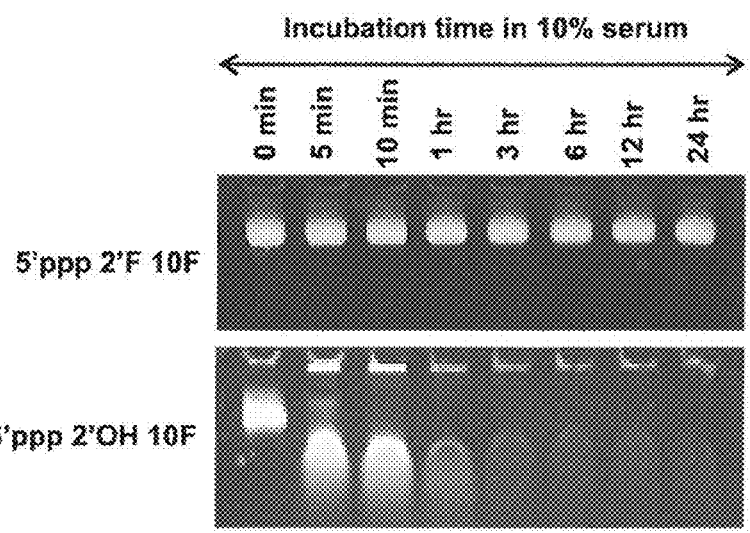
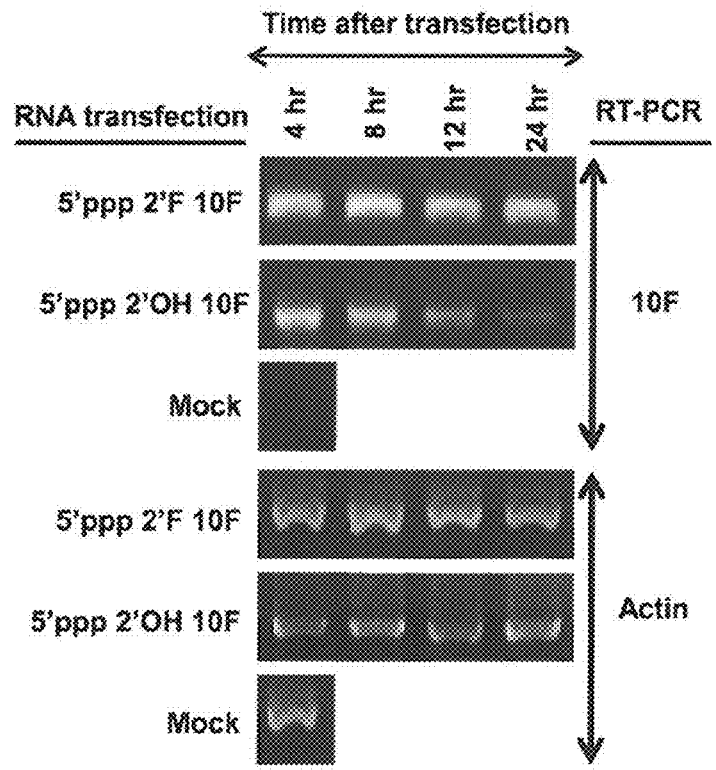

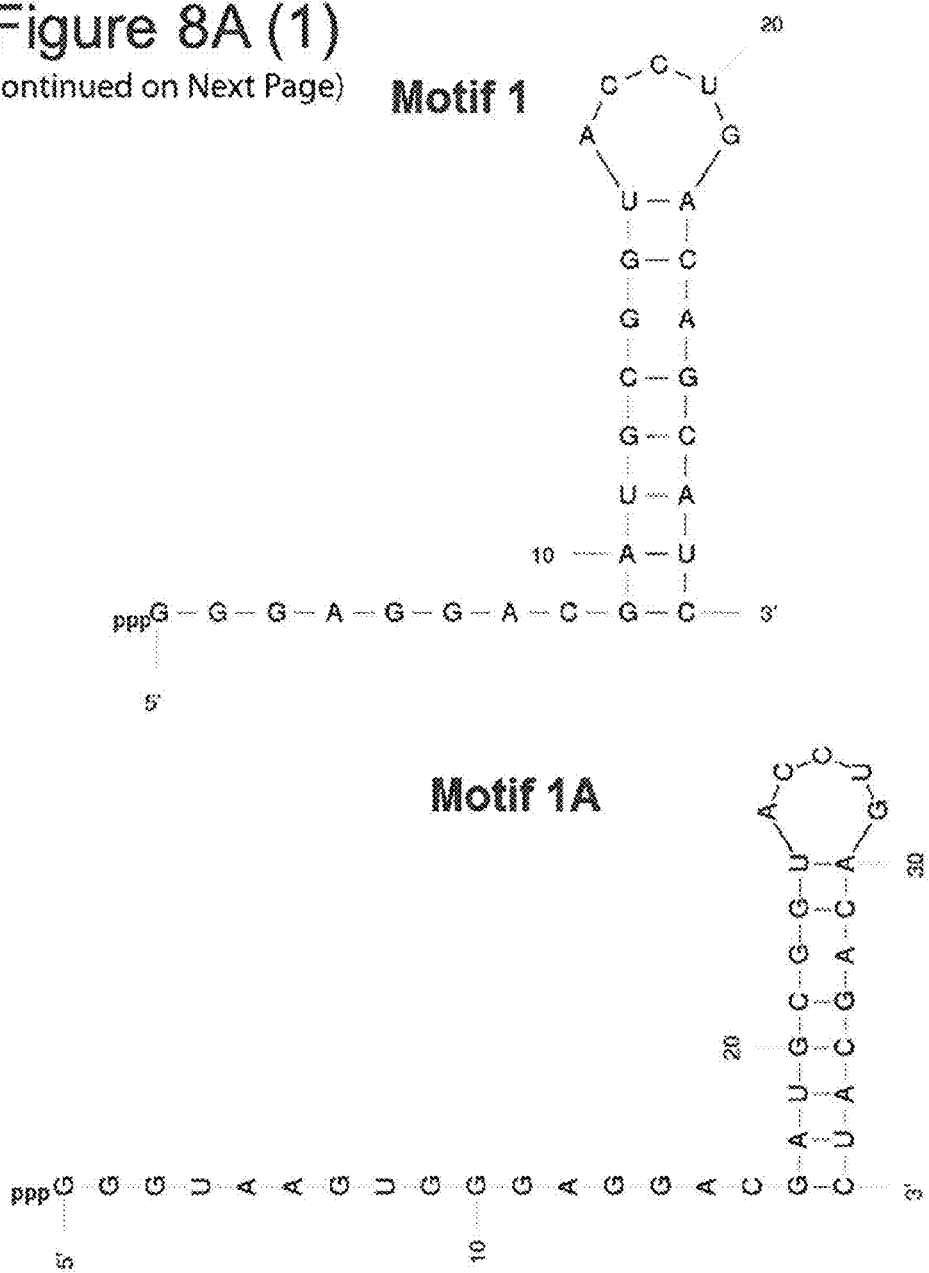
Figure 8A (1)
(Continued on Next Page)

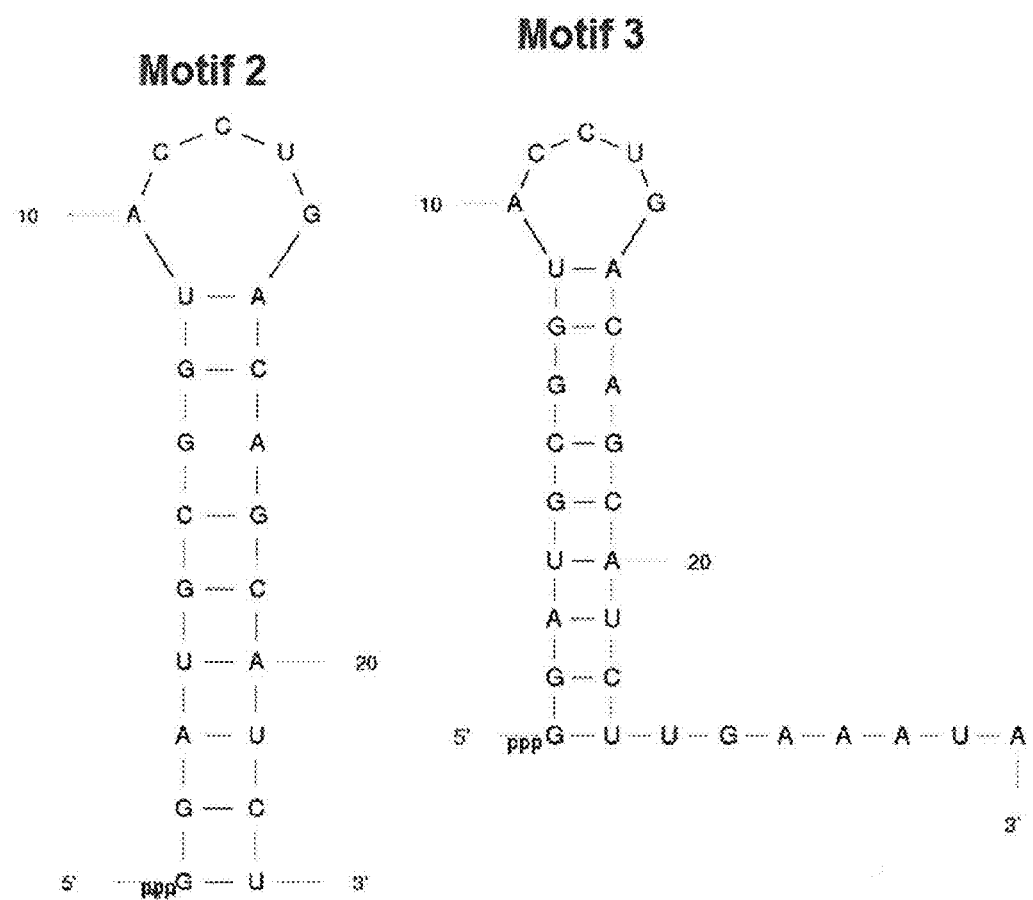
Figure 8A (2) (Continued from Previous Page)

SEQUENCE LISTING

```
<160> NUMBER OF SEQ ID NOS: 17

<210> SEQ ID NO 1
<211> LENGTH: 19
<212> TYPE: RNA
<213> ORGANISM: Artificial Sequence
<220> FEATURE:
<223> OTHER INFORMATION: Synthetic RNA: Guide strand for MAVS siRNA

<400> SEQUENCE: 1
ccaccuugau gccugugaa                                                       19

<210> SEQ ID NO 2
<211> LENGTH: 19
<212> TYPE: RNA
<213> ORGANISM: Artificial Sequence
<220> FEATURE:
<223> OTHER INFORMATION: Synthetic RNA: Guide strand for RIG-I siRNA

<400> SEQUENCE: 2
aucacggauu agcgacaaa                                                       19

<210> SEQ ID NO 3
<211> LENGTH: 19
<212> TYPE: RNA
<213> ORGANISM: Artificial Sequence
<220> FEATURE:
<223> OTHER INFORMATION: Synthetic RNA: Guide strand for MDA5

<400> SEQUENCE: 3
guaucguguu auuggauua                                                       19

<210> SEQ ID NO 4
<211> LENGTH: 71
<212> TYPE: RNA
<213> ORGANISM: Artificial Sequence
<220> FEATURE:
<223> OTHER INFORMATION: Synthetic RNA: Aptamer 10F

<400> SEQUENCE: 4
gggaggacga ugcgguaccu gacagcaucu ugauaauggu ccuacggagc cguuccagac          60
gacucgcccg a                                                               71

<210> SEQ ID NO 5
<211> LENGTH: 71
<212> TYPE: RNA
<213> ORGANISM: Artificial Sequence
<220> FEATURE:
<223> OTHER INFORMATION: Synthetic RNA: Aptamer GPNMB

<400> SEQUENCE: 5
gggaggacga ugcggggaag uacccaaggu cugugaaccc guaaccaugc ggccccagac          60
gacucgcccg a                                                               71

<210> SEQ ID NO 6
<211> LENGTH: 60
<212> TYPE: RNA
<213> ORGANISM: Artificial Sequence
<220> FEATURE:
<223> OTHER INFORMATION: Synthetic RNA: Aptamer 9.14T10

<400> SEQUENCE: 6
gggaggugga cgaacugccc ucagcuacuu ucauguugcu gacgcacaga cgacucgcug          60
```

```
<210> SEQ ID NO 7
<211> LENGTH: 40
<212> TYPE: RNA
<213> ORGANISM: Artificial Sequence
<220> FEATURE:
<223> OTHER INFORMATION: Synthetic RNA: Aptamer 9.14T17

<400> SEQUENCE: 7
gggaggugga cgaacugccc uacgcacaga cgacucgcug                              40

<210> SEQ ID NO 8
<211> LENGTH: 28
<212> TYPE: RNA
<213> ORGANISM: Artificial Sequence
<220> FEATURE:
<223> OTHER INFORMATION: Synthetic RNA: Aptamer 9.14T14

<400> SEQUENCE: 8
gggaggucag cuacuuucau guugcuga                                           28

<210> SEQ ID NO 9
<211> LENGTH: 51
<212> TYPE: RNA
<213> ORGANISM: Artificial Sequence
<220> FEATURE:
<223> OTHER INFORMATION: Synthetic RNA: Aptamer 9.14T13

<400> SEQUENCE: 9
gggaggugcc cucagcuacu uucauguugc ugacgcacag acgacucgcu g                 51

<210> SEQ ID NO 10
<211> LENGTH: 51
<212> TYPE: RNA
<213> ORGANISM: Artificial Sequence
<220> FEATURE:
<223> OTHER INFORMATION: Synthetic RNA: Aptamer FX11-51

<400> SEQUENCE: 10
ggcucggcug ccagcaggus acgagucgca gcgacucgcu gaggauccga g                 51

<210> SEQ ID NO 11
<211> LENGTH: 93
<212> TYPE: RNA
<213> ORGANISM: Artificial Sequence
<220> FEATURE:
<223> OTHER INFORMATION: Synthetic RNA: Aptamer E07

<400> SEQUENCE: 11
ggcgcuccga ccuuagucuc ugugccgcua uaaugcacgg auuuaaucgc cguagaaaag        60
caugucaaag ccggaaccgu guagcacagc aga                                     93

<210> SEQ ID NO 12
<211> LENGTH: 40
<212> TYPE: RNA
<213> ORGANISM: Artificial Sequence
<220> FEATURE:
<223> OTHER INFORMATION: Synthetic RNA: Aptamer LO-1

<400> SEQUENCE: 12
ggggaaguga augggugagg uggaagugag ugagugaaau                              40

<210> SEQ ID NO 13
<211> LENGTH: 30
<212> TYPE: RNA
<213> ORGANISM: Artificial Sequence
<220> FEATURE:
```

-continued

```
<223> OTHER INFORMATION: Synthetic RNA: Aptamer Poly(U)30

<400> SEQUENCE: 13
uuuuuuuuuu uuuuuuuuuu uuuuuuuuuu                                    30

<210> SEQ ID NO 14
<211> LENGTH: 29
<212> TYPE: RNA
<213> ORGANISM: Artificial Sequence
<220> FEATURE:
<223> OTHER INFORMATION: Synthetic RNA: Aptamer Motif 1

<400> SEQUENCE: 14
gggaggacga ugcgguaccu gacagcauc                                     29

<210> SEQ ID NO 15
<211> LENGTH: 37
<212> TYPE: RNA
<213> ORGANISM: Artificial Sequence
<220> FEATURE:
<223> OTHER INFORMATION: Synthetic RNA: Aptamer Motif 1A

<400> SEQUENCE: 15
ggguaagugg gaggacgaug cgguaccuga cagcauc                            37

<210> SEQ ID NO 16
<211> LENGTH: 23
<212> TYPE: RNA
<213> ORGANISM: Artificial Sequence
<220> FEATURE:
<223> OTHER INFORMATION: Synthetic RNA: Aptamer Motif 2

<400> SEQUENCE: 16
ggaugcggua ccugacagca ucu                                           23

<210> SEQ ID NO 17
<211> LENGTH: 30
<212> TYPE: RNA
<213> ORGANISM: Artificial Sequence
<220> FEATURE:
<223> OTHER INFORMATION: Synthetic RNA: Aptamer Motif 3

<400> SEQUENCE: 17
ggaugcggua ccugacagca ucuugaaaua                                    30
```

2-FLUORO-MODIFIED RNAS AS IMMUNOSTIMULATORS

CROSS-REFERENCE TO RELATED APPLICATIONS

This patent application is a national stage filing under 35 U.S.C. 371 of International Application No. PCT/US2014/033518, filed Apr. 9, 2014, which claims the benefit of priority of U.S. Provisional Patent Application No. 61/810,073, filed Apr. 9, 2013, both of which are incorporated herein by reference in their entirety.

STATEMENT REGARDING FEDERALLY SPONSORED RESEARCH

This invention was made with United States government support awarded by the National Institutes of Health, National Cancer institute grant number R011 CA129190. The United States may have certain rights in this invention.

SEQUENCE LISTING

This application is being filed electronically via EFS-Web and includes an electronically submitted Sequence Listing in .txt format. The .txt file contains a sequence listing entitled "2014-04-09_5667-00163_ST25.txt" created on Apr. 9, 2014 and is 4 kilobytes in size. The Sequence Listing contained in this .txt file is part of the specification and is hereby incorporated by reference herein in its entirety.

INTRODUCTION

Pattern-recognition receptors (PRRs) are a pivotal component of both anti-viral and anti-bacterial immunity. These receptors recognize structurally diverse molecules associated with pathogens and stimulate the host immune system against infection (Kawai and Akira (2007) Semin Immunol 19: 24-32). Viral or bacterial RNAs can be recognized as immune stimuli by multiple families of PRRs in the infected cells. Retinoic acid inducible gene-I (RIG-I), melanoma differentiation associated gene-5 (MDA-5) and RNA-activated protein kinase R (PKR) are cytoplasmic double-stranded RNA (dsRNA)-sensing PRRs, while toll-like receptors (TLRs) 3 and 7/8 are localized in endoplasmic compartments and are activated by dsRNA and single-stranded RNA (ssRNA), respectively (Besch et al., (2009) J Clin Invest 119: 2399-2411). PRR signaling, irrespective of which PRR is activated, culminates in the activation of MAP kinases, NF-κB and IFN regulatory factors and engenders the production of inflammatory cytokines (e.g., interleukin (IL)-8) and type I IFN (Tormo et al., (2009) Cancer Cell 16: 103-114).

In addition to anti-infectious immunity, activation of RNA-sensing PRRs can mediate programmed cell death in infected cells, in which case the host can efficiently block viral replication by sacrificing infected cells. Transfection of synthetic long dsRNA (e.g., polyI:C) or short RNAs containing 5' triphosphates (5'ppp) induces type I IFN production and apoptosis of various tumor cells including melanoma, ovarian cancer, acute myeloid leukemia and breast cancer through multiple RNA-sensing PRRs. This PRR-mediated apoptosis can enhance the susceptibility of cancer cells to the cytotoxicity of NK cells and phagocytosis by dendritic cells (DCs), suggesting that PRR-mediated cancer cell apoptosis is pro-immunogenic and can enhance anti-tumor immunity. One caveat of PRR-activating RNA therapeutics is the short half-life of RNA in vivo because RNA is extremely sensitive to serum nucleases. Chemical modifications have been widely used to increase the stability and nuclease resistance of RNAs. RNA ribose modifications, i.e., 2' fluoro (2'F) and 2'-O-methyl (2'O-Me), are the most common type of RNA modification. These ribose-modified RNAs, however, have been shown to evade immune activation by inhibiting the activation of multiple RNA-sensing PRRs. These limitations hamper the development of PRR-activating RNA therapeutics.

SUMMARY

The Examples demonstrate that transfection of human melanoma cells with 2' fluoro (2'F) modified 5' triphosphate (5'ppp) single-stranded RNAs (ssRNAs) induces apoptosis and interferon-β, but not tumor necrosis factor-α production, comparable to transfection with conventional RIG-I agonists. These 2'F 5'ppp ssRNAs elicit RIG-I- and MAVS-mediated apoptosis in a length- and secondary structure-dependent manner.

In one aspect, compositions capable of inducing programmed cell death and cytokine or chemokine production after administration to cells are provided. The compositions include a 5' triphosphate, 2' fluoro-modified pyrimidine non-linear single stranded RNA at least 17 nucleotides long with a least 3 base pairings or a 5' triphosphate, 2' fluoro-modified pyrimidine double stranded RNA at least 17 base pairs long.

In another aspect, methods of inhibiting the growth of cells or inducing cell death are also provided. The cells are contacted with the compositions provided herein in an amount effective to inhibit the growth of the cells, induce programmed cell death or induce cytokine production by the cells.

In a still further aspect, methods of treating subjects with a proliferative disorder, infection, e.g. a viral infection, or in need of immunostimulation are provided. The compositions provided herein may be administered to the subject in an amount effective to treat the disorder in the subject. The compositions of the invention must be delivered to the cells or tissues of the subject and the composition will inhibit the growth of the cells or tissue, induce programmed cell death or induce cytokine production by the cells. The subjects may have a cancer and the 5'ppp 2'F RNAs may be used to induce programmed cell death of the cancer cells.

BRIEF DESCRIPTION OF THE DRAWINGS

FIG. 1 is a set of schematic structures of RNAs used in this study and demonstrates the cytotoxicity of 5'ppp 2'F RNA aptamers in a sequence independent manner. FIG. 1A is a set of schematic secondary structures of 5'ppp 2'F RNA aptamers as predicted with the lowest free energy (ΔG) computed by mfold (http://mfold.rna.albany.edu/?q=mfold/RNA-Folding-Form).

Figure 2:
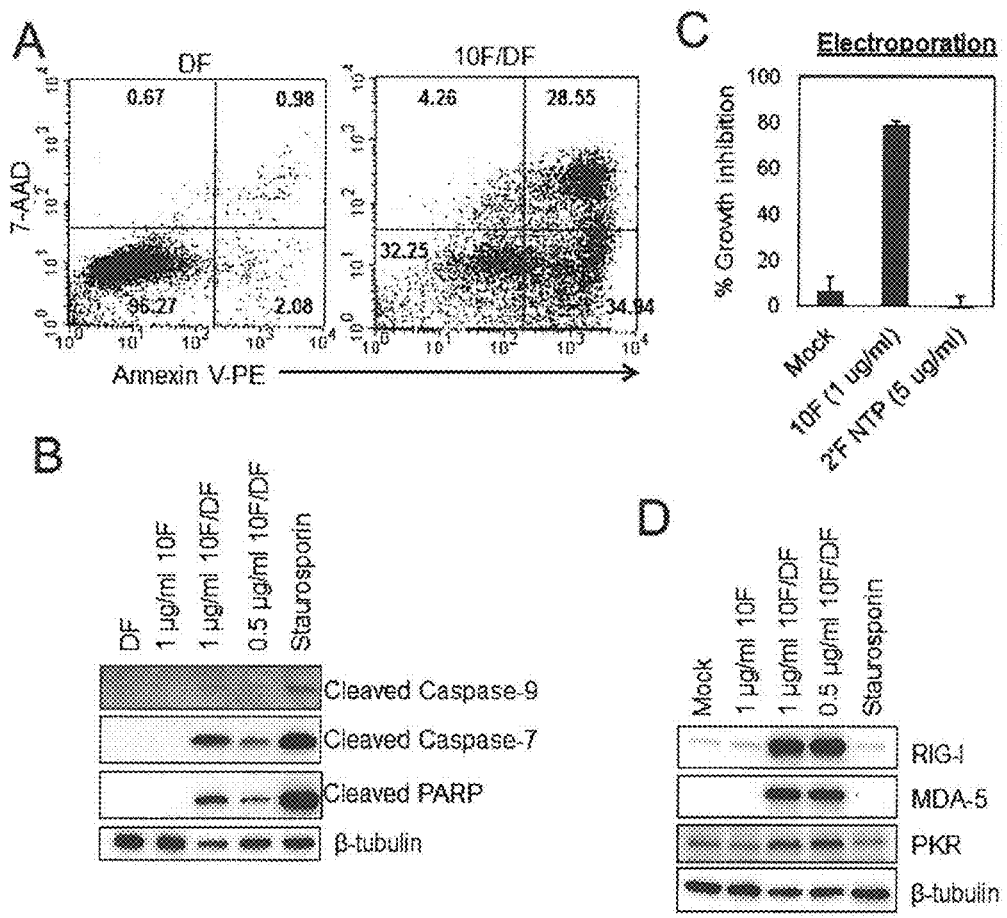

FIG. 2 demonstrates that cytoplasmic delivery of 5'ppp 2'F RNA aptamers into human melanoma cells leads to growth inhibition and induction of apoptosis. FIG. 2A is a set of FACS plots showing induction of apoptosis. WM266-4 cells were incubated with either liposome (DF) alone or 5'ppp 2'F 10F-liposome complex (10F/DF). At 5 h after incubation, cells were replenished with fresh culture medium. Cells were then incubated for an additional 48 hours, harvested and analyzed for cell death. FIG. 2B is a set of Western blots showing activation of caspases and PARP after transfection. WM266-4 cells were either mock-treated, treated with the 5'ppp 2'F 10F without the transfection reagent, or with the 5'ppp 2'F 10F-transfection reagent complex at the indicated concentrations (1 µg/ml or 0.5 µg/ml). The activation of caspase-7, -9, and PARP was assessed by western blot using antibodies specific to the activated (cleaved) proteins (24 h after treatment). Staurosporine-treated cells were used as a positive control. FIG. 2C is a graph showing the percent growth inhibition after the indicated treatment. WM266-4 cells were electroporated with PBS (mock), polyI:C, 5'ppp 2'F 10F or a 2'F pyrimidine nucleoside triphosphate mix (2'F NTP). The growth inhibition was assessed at 72 h after electroporation. FIG. 2D is a set of Western blots showing expression of several proteins after the indicated treatments. WM266-4 cells were treated as in (2B), and the expression of RIG-I, MDA-5, and PKR was analyzed at 24 hours after treatments. Note that β-tubulin levels (loading control) were reproducibly reduced in cells treated with 5'ppp 2'F 10F/DF complex. The data represent two individual experiments. Error bars are S.D.

FIG. 3 is a set of graphs showing that transfection of 5'ppp 2'F ssRNAs does not stimulate TLR3 and TLR7. FIG. 3A shows that TLR3 is not stimulated. The human TLR3 reporter cell, HEK-hTLR3-NFκB/SEAP was purchased from Invivogen. These cells were stably co-transfected with the human TLR3 gene and an inducible SEAP (secreted embryonic alkaline phosphatase) reporter gene into HEK293 cells. The SEAP gene is placed under the control of NF-κB and AP-1. HEK-hTLR3-NFκB/SEAP cells were specifically stimulated with TLR3 ligands including polyI:C and polyI:C-DF complex, but not with DF alone, 5'ppp 2'F 10F-DF complexes and TLR7 agonist R848. SEAP gene expression was measured using the SEAP detection media QUANTI-BLUE (Invivogen), according to the manufacturer's instructions. FIG. 3B is a graph showing that TLR7 is not stimulated by the ssRNAs. Human TLR7-expressing HEK293 cells were kindly provided by Dr. Todd Brennan (Duke University, Durham, N.C.). Treatment with R848 but not with polyI:C, polyI:C-DF and 5'ppp 2'F 10F-DF complexes stimulated HEK-TLR7 cells to produce the inflammatory cytokine IL-8. The data represent the mean of two experiments. Error bars represent the S.D.

Figure 4:
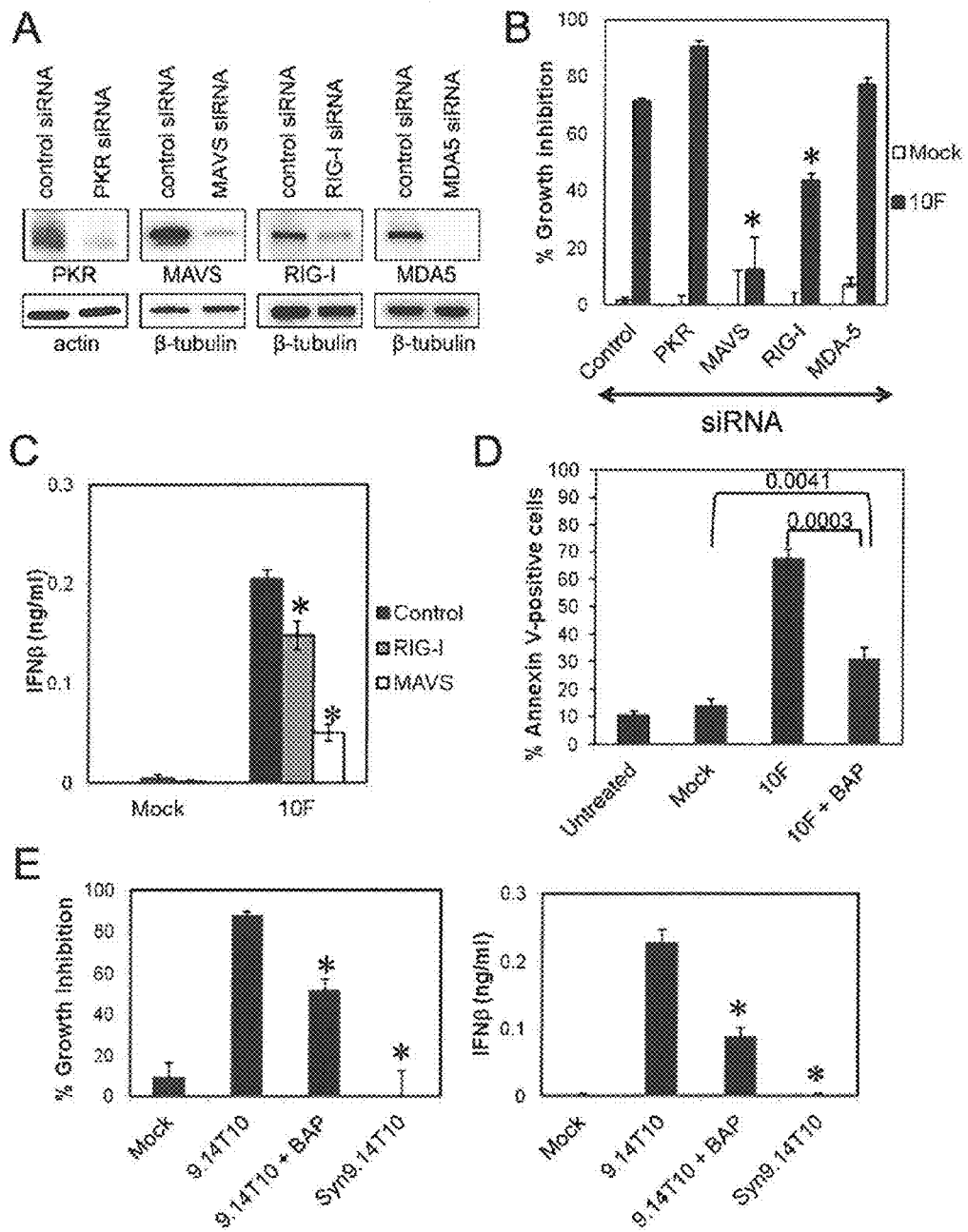

FIG. 4 is a set of data showing that 5'ppp 2'F ssRNA-induced cell death and growth inhibition of melanoma cells are dependent on cytoplasmic RIG-I and MAVS. FIG. 4A is a set of western blots showing knockdown of the indicated proteins. WM266-4 cells were transfected twice at 2-day intervals with either control 5'OH siRNA or 5'OH siRNAs against PKR, RIG-I, MDA-5 and MAVS. The knockdown efficiency was assessed 4 days after siRNA transfections by western blot using specific antibodies (as indicated; upper panel). Probing of the same membrane with either actin- or β-tubulin-specific antibodies served as loading controls (lower panel). FIGS. 4B and C are a set of graphs showing that MAVS and RIG-I are required for cell growth inhibition and cytokine production by ssRNA. WM266-4 cells treated as in (A) were either further treated with transfection reagent alone (mock), or 10F-transfection reagent complex (10F) (0.125 µg/ml) at 24 hours after the last siRNA transfection. The growth inhibition (FIG. 4B and IFNβ production (FIG. 4C) were analyzed at 72 h after 10F treatment. FIGS. 4D and E are a set of graphs showing the ability to partially reverse the effect of the ssRNA by treatment with a phosphatase to dephosphorylate the ssRNA. 5'ppp 2'F 10F (FIG. 4D) and 5'ppp 2'F 9.14T10 (FIG. 4E) was dephosphorylated by incubation with bacterial alkaline phosphatase (BAP). In addition, 5'OH-2'F 9.14T10 (Syn9.14T10) was non-enzymatically synthesized to completely remove the 5'ppp. The apoptosis, cytotoxic effect and IFNβ expression of WM266-4 cells treated with mock, 10F or dephosphorylated 10F (0.125 µg/ml each) was determined by flow cytometry after staining cells with Annexin V-PE, MTT assay and IFNβ ELISA, respectively. The data represent two individual experiments. Error bar represent the S.D.; * P<0.05.

FIG. 5 is a set of graphs showing IFNβ-dependent and independent mechanisms contribute to 5'ppp 2'F ssRNA-induced growth inhibition of human cancer cells. FIG. 5A is a graph showing the growth inhibition is mediated at least in part by IFN-β. The human melanoma cell line, WM266-4 and human dermal fibroblasts were transfected with 10F or mock transfected in the presence (empty bars) and absence (filled bars) of B18R, the vaccinia virus-encoded type I IFN decoy receptor. In parallel, the culture supernatants of cells transfected with either mock or 10F were harvested after 24 h. Fresh melanoma cells and dermal fibroblasts were incubated for 72 h with the culture supernatants in the presence and absence of B18R. The growth inhibition of WM266-4 cells treated with IFNβ in the presence and absence of B18R was used as an experimental control. FIG. 5B is a graph showing that not all cells are susceptible to ssRNA mediated growth inhibition. A variety of human cancer cell lines and normal human cells were either transfected with 5'ppp 2'F 10F (0.5 µg/ml) or treated with transfection reagent only (mock), and the growth inhibition relative to untreated cells was analyzed at 72 h after transfection by an MTT assay. Error bars represent the S.D. * P<0.05 (5'ppp 2'F 10F vs Mock).

FIG. 6 is a set of graphs showing that 2'F modification increases nuclease resistance, cytotoxicity and inflammatory cytokine induction of immunostimulatory 5'ppp ssRNAs. FIG. 6A is a graph showing ability of various modified ssRNAs to inhibit the growth of cells over concentration ranges. WM266-4 cells were treated with transfection reagent alone (mock) or the complex of transfection reagent and 5'ppp 10F containing 2'F pyrimidine, 2'OMe pyrimidine or unmodified pyrimidine (2'OH) at various concentrations. The viral dsRNA analog PolyI:C was used as an experimental control. Growth inhibition was assessed at 72 h post treatments using the MTT assay. FIG. 6B is a set of graphs showing cytokine induction after treatment with the indicated ssRNAs. WM266-4 cells were either treated with transfection reagent alone (mock) or the complex of transfection reagent and 5'ppp 2'OH 10F, 5'ppp 2'F 10, 5'ppp 2'OMe 10F or poly I:C (0.5 µg/ml each). The secretion of IFNβ and IL-8 by the melanoma cells was analyzed at 24 h after treatment by ELISA. The data represent the mean of three experiments. Error bars represent the S.D.; * P<0.05 (5'ppp 2'F 10F vs 5'ppp 2'OH 10F); P<0.001 (5'ppp 2'OMe 10F vs 5'ppp 2'OH 10F). FIG. 6C is a photograph of a gel showing the serum stability of 2'F and 2'OH ssRNAs. 5'ppp 2'OH 10F and 5'ppp 2'F 10F were incubated in 10% fetal bovine serum at 37° C. for 0, 5 min, 10 min, 1 h, 3 h, 6 h, 12 h or 24 h and collected at each time point. RNAs were analyzed on 12% polyacrylamide gels. FIG. 6D is a photograph of a gel showing the cellular stability of 2'F and 2'OH ssRNAs. WM266.4 cells were transfected with 5'ppp 2'OH 10F, 5'ppp 2'F 10F or mock. At 4 h, 8, 12 and 24 h after transfection, total RNAs were isolated and cellular 10F RNA levels were analyzed by RT-PCR. Actin mRNA levels were used as an internal control. The data represent three individual experiments.

Figure 7:
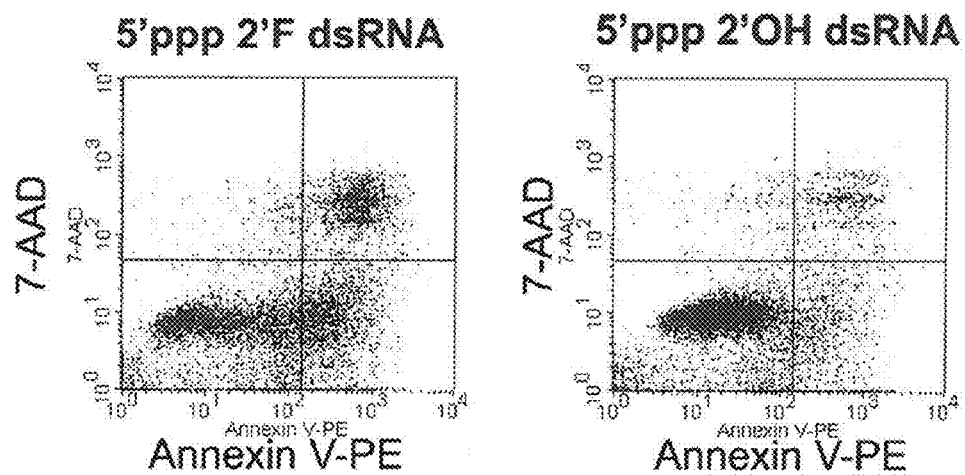

FIG. 7 is a set of FACS analysis plots showing the induction of apoptosis by 5'ppp-2'F small dsRNA after transfection of melanoma cells. 2'F modification may improve anti-cancer activity of conventional RIG-I agonist 5'ppp dsRNA. Transfection of 5'ppp-2'F short dsRNA increased apoptosis of human melanoma cells as compared to unmodified 5'ppp-2'OH dsRNA.

Figures 8B, 8C:
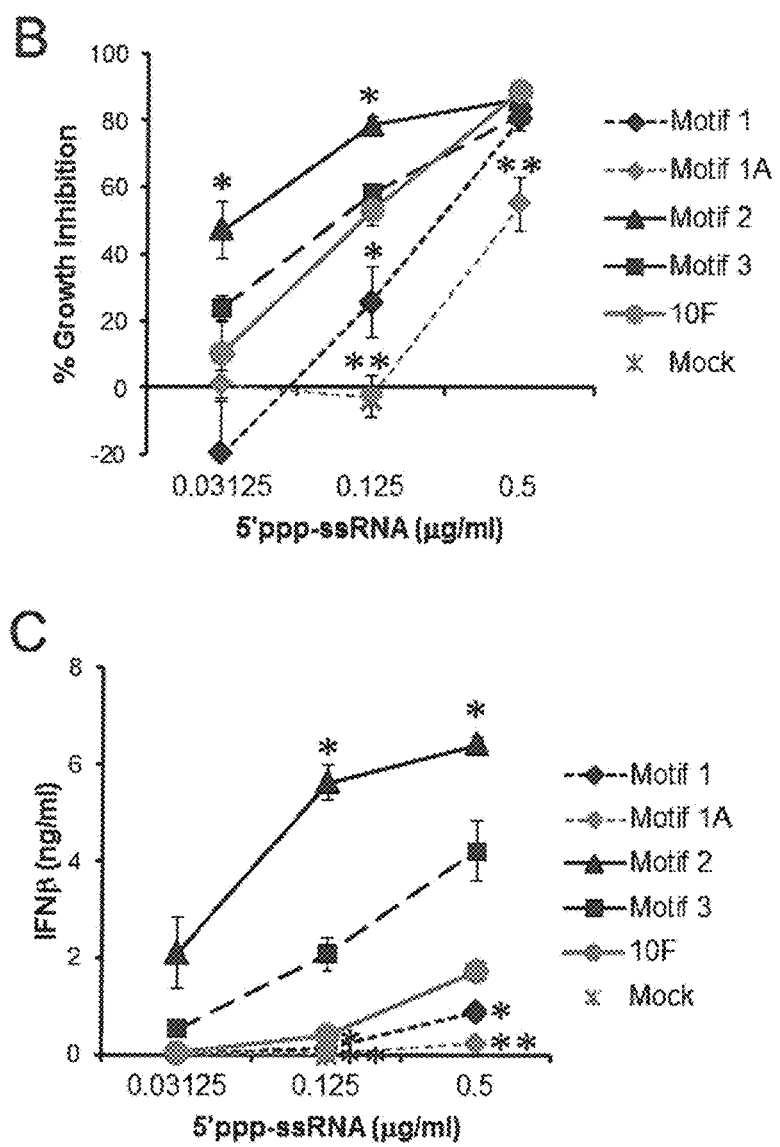

FIG. 8 is a set of structures and graphs showing that the distance between 5'ppp and internal stem structure of 5'ppp 2'F ssRNAs is inversely correlated to cytotoxic effect and IFN-β expression in human melanoma cells. FIG. 8A shows the mfold-predicted structures of 5'ppp 2'F stem-loop ssRNAs consisting of 5'overhang (Motif 1 (SEQ ID NO: 14) and 1A (SEQ ID NO: 15)), blunt end (Motif 2 (SEQ ID NO: 16)) and 3'overhang (Motif 3 (SEQ ID NO: 17)). Only one secondary structure was predicted for individual ssRNA by mfold with negative ΔG. FIGS. 8B and C are graphs showing the effect of transfection of melanoma cells with each of the indicated ssRNA on growth inhibition and cytokine production. WM266-4 cells were transfected with Motif 1, Motif 1A, Motif 2, Motif 3 or 10F at the indicated concentrations. Cytotoxicity (FIG. 8B) and IFNβ production (FIG. 8C) by the cells were evaluated by MTT assay and IFNβ ELISA, respectively. The data represent the mean of three experiments. Error bars represent the S.D.; * P<0.05, compared to 10F; ** P<0.05, Motif 1 vs Motif 1A.

DETAILED DESCRIPTION

Compositions capable of inducing programmed cell death, type I interferon (interferon-β) and inflammatory cytokine production by cells or activation of Pattern Recognition Receptors (PRR) in cells are provided and described herein. The compositions include a 5' triphosphate, 2' fluoro-modified pyrimidine non-linear single-stranded RNA (ssRNA) or double-stranded RNA (dsRNA) at least 17 nucleotides long. As described in the Examples, multiple 2'F RNA aptamers harboring a 5'ppp that specifically binds to target molecules in the cells were generated. Surprisingly, intra-cytoplasmic delivery of these RNA aptamers elicits potent cytotoxicity and type I IFN production by human melanoma, prostate cancer and glioblastoma cells. This RNA aptamer-mediated cell death and IFN production is specific to cancer cells and did not inhibit cell growth of various non-cancer cells other than melanocytes. Furthermore, these effects are dependent on 5'ppp, 2'F modification and the secondary structures of the RNA aptamers. These effects were demonstrated to be sequence independent. Finally, the 5'ppp 2'F RNA aptamer-induced melanoma cell death is dependent on the activation of cytoplasmic pattern recognition receptors (e.g., RIG-I) and the downstream adaptor molecule, mitochondrial antiviral-signaling protein (MAVS).

As noted the RNAs are suitably at least 17 nucleotides long and are suitably no more than 200 nucleotides long. The RNAs may be between 17, 18, 19, 20, 25, 30, 35, 40, 45, 50, 55, 60, or 65 nucleotides and 200, 180, 160, 150, 140, 130, 120, 110, 100 or 90 nucleotides long. In the Examples at least one 2' Fluoro modification in the RNA was needed to inhibit growth of cells. Suitably, the 2' fluoro-modification is present on at least 10%, 20%, 30%, 40%, 50%, 60%, 70%, 80%, 90% or more of the pyrimidines, suitably the modified pyrimidines are uridines. In one embodiment, all of the uridines in the RNA are 2' fluoro-modified. In another embodiment, all of the pyrimidines in the RNA are 2' fluoro-modified. The 5' end of the RNA must be a 5' triphosphate for the composition to function in the methods.

In the Examples, linear RNAs were not effective at inhibiting cell growth, while those with secondary structure were capable of inhibiting cell growth. Thus, suitably the RNAs in the composition form a secondary structure with a double-stranded portion. Suitably, the RNA is capable of forming single or multiple stem loop structures. The double-stranded portion of the RNA should include at least 3, 4, 5, 6, 7, 8, 9, 10, 11, 12, 13, 14, 15, 16, 17, 18, 19, 20, 21, 22, 23, 24 25 or more base pairs. The double stranded portion of the RNA is suitably positioned within 15, 14, 13, 12, 11, 10, 9, 8, 7, 6, 5, 4, 3, 2, 1 nucleotides of or at the 5' end of the RNA. Double-stranded RNA with 2' fluoro and 5' triphosphate are also useful in the methods of immunostimulation and induction of programmed cell death described herein. The dsRNA should also be between 17, 18, 19, 20, 25, 30, 35, 40, 45, 50, 55, 60, or 65 base pairs and 200, 180, 160, 150, 140, 130, 120, 110, 100 or 90 base pairs long.

The compositions described herein may also include a cytoplasmic delivery mechanism. The RNAs in the compositions must be delivered into the cells or produced within the cells to function. As shown in the Examples, extracellular administration of the RNA containing compositions without a delivery mechanism resulted in a lack of effectiveness. Such delivery mechanisms are available to those skilled in the art and include all gene delivery mechanisms including but not limited to synthetic polymers (such as those used for siRNA delivery), cell-penetrating peptides (such as VP16), nanoparticles, viral or liposomal delivery to the cytoplasm of cells (lipofection), delivery via a gene gun, or may include transfection, nucleofection or electroporation. The cytoplasmic delivery mechanisms may be targeted to only deliver the compositions to cells in which cell growth inhibition or induction of programmed cell death is desired. For example, the cellular delivery mechanism may specifically target the RNAs to cancer cells or virally infected cells. The compositions may be targeted to cells for uptake by receptor-mediated endocytosis as well. As shown in the examples, most non-cancerous cells are not susceptible to these RNAs so targeting may not be needed in some systems, but may be useful to obtain sufficient delivery to the target cells. In addition, cells could be genetically engineered to express the RNA compositions described herein. The RNAs could be operably connected to a promoter, such as an inducible promoter, to allow expression of the RNA only upon proper stimulation.

The compositions described herein may also be used to inhibit cancer cell growth or induce programmed cell death of cancer cells which may result in treating cancer in a subject. The compositions may also be useful in treating other non-cancerous proliferative disorders or in treating infected cells, such as cells infected with a virus or other intracellular pathogen. The compositions provided herein may also be administered as an adjuvant to stimulate an immune response to an antigen, pathogen or cancer cell. Subjects that may be administered the compositions described herein include, but are not limited to mammals, domesticated animals and humans and may specifically include dogs, cats, fish, chickens, cows, pigs, sheep, goats.

Along these lines, methods of inhibiting the growth of cells or inducing programmed cell death using the compositions comprising the ssRNAs or dsRNAs described herein are also provided. The methods include contacting cells with the compositions or alternatively administering the compositions to subjects in an amount effective to inhibit the growth of cells, induce programmed cell death of cells or increase inflammatory cytokine production by cells. The inhibition of growth of the cells or induction of cell death is independent of the nucleotide sequence of the RNA, is partially dependent on induction of type I interferons (IFN-β), activation of pattern recognition receptors (RIG-I) and induction of MAVS, independently. The type I interferons (IFN-β) may have autocrine or paracrine effects on cells. Other cytokines such as IL-8 are also induced in the cells treated with the RNA compositions described herein. The cells may be melanoma cells, or other cancer cells, including but not limited to brain, prostate, ovarian, renal, lung, liver, colorectal and breast cancer cells or leukemia or lymphoma cells.

Suitably, the composition is delivered to the cytoplasm of the cell. The compositions may be delivered through the cytoplasmic delivery mechanisms described above and include but are not limited to liposomes, synthetic polymers, cell penetrating peptides, nanoparticles, viral encapsulation, receptor-mediated endocytosis, electroporation or any other means to deliver the composition to the cytoplasm of the cells.

Cells may be contacted with the composition directly or indirectly in vivo, in vitro, or ex vivo. Contacting encompasses administration to a cell, tissue, mammal, patient, or human. Further, contacting a cell includes adding the composition to a cell culture with a cytoplasmic delivery mechanism or introducing the composition into the cytoplasm of the cell via any available means. Other suitable methods may include introducing or administering the composition to a cell, tissue, mammal, or patient using appropriate procedures and routes of administration as defined below.

Administration of the compositions described herein may inhibit the growth of cancer cells or treat cancer. This effect may be due to a general immunostimulatory effect of administration of the compositions or by programmed cell death initiated by contact with the compositions. The administration of the compositions described herein may inhibit the growth of the cells by 20%, 30%, 40%, 50%, 60%, 65%, 70%, 75%, 80% or more as compared to control treated cells. The administration of the compositions described herein may also induce cell death, suitably programmed cell death in 5%, 100%, 15%, 20%, 25%, 30%, 35%, 40%, 45%, 50%, 55%, 60%, 65%, 70% or more than 75% of the treated cells. Programmed cell death includes any means of cell death mediated by an intracellular program and includes, but is not limited ot apoptosis, autophagy, necroptosis, anoikis, or other non-apoptotic forms of programmed cell death. Suitably, administration to a subject or contacting cells with the compositions described herein increases the amount of type I interferon (IFN α or IFN β) and IL-8 produced by the cells. Suitably the cytokine are increased 2, 3, 4, 5, 7, 10, or more fold as compared to the production of these cytokines in untreated control cells.

The compositions described herein may be administered to a subject to treat cancer in the subject. Treating cancer includes, but is not limited to, reducing the number of cancer cells or the size of a tumor in the subject, reducing progression of a cancer to a more aggressive form, reducing proliferation of cancer cells (inhibiting the growth of) or reducing the speed of tumor growth, killing of cancer cells (via any means), reducing metastasis of cancer cells or reducing the likelihood of recurrence of a cancer in a subject. Treating a subject as used herein refers to any type of treatment that imparts a benefit to a subject afflicted with a disease or at risk of developing the disease, including improvement in the condition of the subject (e.g., in one or more symptoms), delay in the progression of the disease, delay the onset of symptoms or slow the progression of symptoms, etc.

The compositions may be used to make pharmaceutical compositions. Pharmaceutical compositions comprising the RNAs and compositions described above and a pharmaceutically acceptable carrier are provided. A pharmaceutically acceptable carrier is any carrier suitable for in vivo administration. Examples of pharmaceutically acceptable carriers suitable for use in the composition include, but are not limited to, water, buffered solutions, glucose solutions, oil-based or bacterial culture fluids. Additional components of the compositions may suitably include, for example, excipients such as stabilizers, preservatives, diluents, emulsifiers and lubricants. Examples of pharmaceutically acceptable carriers or diluents include stabilizers such as carbohydrates (e.g., sorbitol, mannitol, starch, sucrose, glucose, dextran), proteins such as albumin or casein, protein-containing agents such as bovine serum or skimmed milk and buffers (e.g., phosphate buffer). Especially when such stabilizers are added to the compositions, the composition is suitable for freeze-drying or spray-drying. The composition may also be emulsified.

The compositions described herein may also be combined with a chemotherapeutic or other therapy for treatment of a disease or condition or in conjunction with an antigen to stimulate a more effective immune response against the antigen or a pathogen comprising the antigen. An antigen includes any peptide, carbohydrate or lipid to which an immune response can be generated. In particular the antigen is capable of stimulating a B cell or T cell immune response such that a memory response is generated. The compositions may be administered in any order, at the same time or as part of a unitary composition. The composition described herein and the therapeutic may be administered such that one is administered before the other with a difference in administration time of 1 hour, 2 hours, 4 hours, 8 hours, 12 hours, 16 hours, 20 hours, 1 day, 2 days, 4 days, 7 days, 2 weeks, 4 weeks or more.

An effective amount or a therapeutically effective amount as used herein means the amount of the composition that, when administered to a subject for treating a state, disorder or condition, such as cancer, is sufficient to effect a treatment (as defined above). The therapeutically effective amount will vary depending on the composition, the disease and its severity and the age, weight, physical condition and responsiveness of the subject to be treated.

The compositions described herein may be administered by any means known to those skilled in the art, including, but not limited to, oral, topical, intranasal, intraperitoneal, parenteral, intravenous, intracranial, intratumoral, intramuscular, subcutaneous, intrathecal, transcutaneous, nasopharyngeal, or transmucosal absorption. Thus the compositions may be formulated as an ingestable, injectable, topical or suppository formulation. The compositions may also be delivered with in a lipoplex, polyplex, target-specific nanoparticle or time-release vehicle. Administration of the compositions to a subject in accordance with the invention appears to exhibit beneficial effects in a dose-dependent manner. Thus, within broad limits, administration of larger quantities of the composition is expected to achieve increased beneficial biological effects than administration of a smaller amount. Moreover, efficacy is also contemplated at dosages below the level at which toxicity is seen.

It will be appreciated that the specific dosage administered in any given case will be adjusted in accordance with the compositions being administered, the disease to be treated or inhibited, the condition of the subject, and other relevant medical factors that may modify the activity of the composition or the response of the subject, as is well known by those skilled in the art. For example, the specific dose for a particular subject depends on age, body weight, general state of health, diet, the timing and mode of administration, the rate of excretion, medicaments used in combination and the severity of the particular disorder to which the therapy is applied. Dosages for a given patient can be determined using conventional considerations, such as by means of an appropriate conventional pharmacological or prophylactic protocol.

The maximal dosage for a subject is the highest dosage that does not cause undesirable or intolerable side effects. The number of variables in regard to an individual prophylactic or treatment regimen is large, and a considerable range of doses is expected. The route of administration will also impact the dosage requirements. It is anticipated that dosages of the composition will reduce symptoms of the condition at least 10%, 20%, 30%, 40%, 50%, 60%, 70%, 80%, 90% or 100% compared to pre-treatment symptoms or symptoms is left untreated. It is specifically contemplated that pharmaceutical preparations and compositions may palliate or alleviate symptoms of the disease without providing a cure, or, in some embodiments, may be used to cure the disease or disorder.

Suitable effective dosage amounts for administering the compositions may be determined by those of skill in the art, but typically range from about 1 microgram to about 100,000 micrograms per kilogram of body weight weekly, although they are typically about 1,000 micrograms or less per kilogram of body weight weekly. In some embodiments, the effective dosage amount ranges from about 10 to about 10,000 micrograms per kilogram of body weight weekly. In another embodiment, the effective dosage amount ranges from about 50 to about 5,000 micrograms per kilogram of body weight weekly. In another embodiment, the effective dosage amount ranges from about 75 to about 1,000 micrograms per kilogram of body weight weekly. The effective dosage amounts described herein refer to total amounts administered, that is, if more than one composition is administered, the effective dosage amounts correspond to the total amount administered. The composition can be administered as a single dose or as divided doses. For example, the composition may be administered two or more times separated by 4 hours, 6 hours, 8 hours, 12 hours, a day, two days, three days, four days, one week, two weeks, or by three or more weeks.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The following examples are meant only to be illustrative and are not meant as limitations on the scope of the invention or of the appended claims.

EXAMPLES

Materials and Methods

Cell Culture

WM266-4, WM115, SK-MEL-2 and normal human colon epithelial cells (all from ATCC, Manassas, Va.) were maintained in Eagle's Minimum Essential Medium supplemented with 10% FBS, 1× Non-essential Amino Acid Solution, and 1 mM sodium pyruvate (all from Invitrogen, Carlsbad, Calif.). MALME-3M, DU145, LNCaP, HeLa, Hs578T. HT1080, LN-229, A-172, human lung fibroblast and human bone marrow stromal cell (all from ATCC), Panc-1 (gift from Dr. Rebekah White at Duke University, Durham, N.C.), normal human dermal fibroblast (Invitrogen) were maintained in Dulbecco's Modified Eagle's Medium (DMEM) (Invitrogen) supplemented with 10% FBS. SK-OV-3 (ATCC) was maintained in McCoy's 5A medium (Invitrogen) with 10% FBS. Xeno-43 (gift from Dr. Darell D. Bigner, Duke University) was maintained in Zinc Option Media (Invitrogen). Normal human epidermal melanocytes (ATCC) were maintained in Dermal Cell Basal Medium (ATCC) supplemented with the Adult Melanocyte Growth Kit (ATCC). HPDE cells (gift from Dr. Rebekah White at Duke University) were maintained in Keratinocyte-SFM (Invitrogen). PC3, NCI-H1838 and peripheral blood mononuclear cells (PBMCs) were maintained in RPMI 1640 (Invitrogen) with 10% FBS, HEPES and 1 mM sodium pyruvate. Cells were incubated at 37° C. in a humidified atmosphere with 5% $CO_2$.

Generation of Immunostimulatory and Cytotoxic RNAs

All 2'F-modified and unmodified ssRNAs used in this study were established by in vitro transcription from DNA templates using the Y639F mutant T7 RNA polymerase, as previously described (Layzer and Sullenger (2007) Oligonucleotides 17: 1-11). Unmodified and 2'F-modified ribonucleoside triphosphates were used at a 1 mM and 3 mM final concentration, respectively, in the in vitro transcription reaction. 2'OMe-modified RNA was transcribed from DNA templates using the Y639F/H784A double mutant T7 RNA polymerase (Padilla and Sousa (2002) Nucleic Acids Res 30: e138). Unmodified and 2'OMe-modified ribonucleoside triphosphates were used at 3 mM in the in vitro transcription reaction. The von Willebrand Factor-specific aptamer vWF 9.14 derivatives, 9.14T10 and 9.14T17, were previously reported (Nimjee et al. (2012) Mol Ther 20: 391-397). Aptamer E07 specifically binds to human epidermal growth factor receptor (EGFR) (Li et al. (2011) PLoS One 6: e20299). The human melanocytic cell-targeting aptamer 10F has been selected by ex vivo cell-based SELEX. The transmembrane glycoprotein NMB-specific aptamer GPNMB has been selected for affinity binding to human GPNMB by in vitro SELEX. The coagulation factor XII-specific aptamer FXII-51 was provided by Dr. Becky Smock (Duke University). PolyI:C was purchased from Invivogen, San Diego, Calif. 5'ppp-2'F Poly(U)30 and 5'OH-2'F 9.14T10 were non-enzymatically synthesized by TriLink, San Diego, Calif. siRNAs with 3' TT overhangs for knockdown studies were purchased from Invitrogen and had the guide strand sequences 5'-CCACCUUGAUGCCUGUGAA-3' (for MAVS; SEQ ID NO: 1), 5'-AUCACGGAUUAGCGA-CAAA-3' (for RIG-I; SEQ ID NO: 2), and 5'-GUAUCGU-GUUAUUGGAUUA-3' (for MDA5; SEQ ID NO: 3). The anti-PKR siRNA was purchased as a pool of three target specific 19-25 nt siRNAs from Santa Cruz Biotechnology (Dallas, Tex.). The sequences of the aptamers used in this study are provided in Table 1.

TABLE 1

| 5'ppp-2'F ssRNA sequences | | | |
|---|---|---|---|
| Aptamer | Length | Target | Sequence (SEQ ID NO:) |
| 10F | 71 | Melanoma/ melanocyte | GGGAGGACGAUGCGGUACCUGACAGCAUCUUGAUAAUGG UCCUACGGAGCCGUUCCAGACGACUCGCCCGA (SEQ ID NO: 4) |
| GPNMB | 71 | Glioblastoma | GGGAGGACGAUGCGGGGAAGUACCCAAGGUCUGUGAACC CGUAACCAUGCGGCCCCAGACGACUCGCCCGA (SEQ ID NO: 5) |
| 9.14T10 | 60 | von Willebrand Factor (vWF) | GGGAGGUGGACGAACUGCCCUCAGCUACUUUCAUGUUGC UGACGCACAGACGACUCGCUG (SEQ ID NO: 6) |
| 9.14T17 | 40 | vWF | GGGAGGUGGACGAACUGCCCUACGCACAGACGACUCGCU G (SEQ ID NO: 7) |
| 9.14T14 | 28 | vWF | GGGAGGUCAGCUACUUUCAUGUUGCUGA (SEQ ID NO: 8) |
| 9.14T13 | 51 | vWF | GGGAGGUGCCCUCAGCUACUUUCAUGUUGCUGACGCACA GACGACUCGCUG (SEQ ID NO: 9) |
| FX11-51 | 51 | Coagulation Factor 11 | GGCUCGGCUGCCAGCAGGUCACGAGUCGCAGCGACUCGC UGAGGAUCCGAG (SEQ ID NO: 10 |
| E07 | 93 | EGFR | GGCGCUCCGACCUUAGUCUCUGUGCCGCUAUAAUGCACG GAUUUAAUCGCCGUAGAAAAGCAUGUCAAAGCCGGAACC GUGUAGCACAGCAGA (SEQ ID NO: 11) |
| Poly(U)30 | 30 | None | UUUUUUUUUUUUUUUUUUUUUUUUUUUUUU (SEQ ID NO: 13) |

TABLE 1-continued

5'ppp-2'F ssRNA sequences

| Aptamer | Length | Target | Sequence (SEQ ID NO:) |
|---|---|---|---|
| Motif 1 | 29 | None | GGGAGGACGAUGCGGUACCUGACAGCAUC (SEQ ID NO: 14) |
| Motif 1A | 37 | None | GGGUAAGUGGGAGGACGAUGCGGUACCUGACAGCAUC (SEQ ID NO: 15) |
| Motif 2 | 23 | None | GGAUGCGGUACCUGACAGCAUCU (SEQ ID NO: 16) |
| Motif 3 | 30 | None | GGAUGCGGUACCUGACAGCAUCUUGAAAUA (SEQ ID NO: 17) |

Induction of Innate Immune Responses and Apoptosis by Intracellular Delivery of RNAs For the intracellular delivery of immune stimulatory RNAs, RNAs were transfected with the DharmaFECT® Duo liposomal transfection reagent (Thermo Scientific, Waltham, Mass.) at a transfection reagent (μl):RNA (μg) ratio of 3.75:1, according to the manufacturer's instructions. Unless otherwise stated, for the induction of innate immune responses and apoptosis, immune stimulatory RNAs (500 ng/ml) were transfected into 50 to 70% confluent cells. Cells were incubated with an RNA-transfection agent complex for 5 h, followed by replenishment with fresh culture medium. To electroporate cells, $1\times10^5$ cells suspended in 200 μl Opti-MEM I (Invitrogen) were mixed with 1 μg of immune stimulatory RNAs or 5 μg of 2'Fluoro pyrimidine ribonucleoside triphosphate in 2-mm cuvettes and were electroporated at 300 V for 500 μs using an Electro Square Porator ECM 830 (BTX, San Diego, Calif.). For the knockdown of RNA-sensing PRRs, cells were transfected with PRR-specific siRNAs (25 nM) twice at 2-day intervals using DharmaFECT®-1 (Thermo Scientific). At 5 h after the second siRNA transfection, cells were harvested, replated into a 96-well plate and incubated overnight. Cells were then treated with immune stimulatory RNA transfections. Staurosporine (2 μM) (Sigma, St Louis, Mo.) and recombinant human IFNβ (20 ng/ml) (PeproTech, Rocky Hill, N.J.) were used as positive controls of anti-melanoma cytotoxicity. B18R (100 ng/ml) (eBioscience, San Diego, Calif.) was added directly to the growth media of cells to neutralize IFNβ.

Quantification of Growth Inhibition and Apoptosis

Growth inhibition relative to untreated cells was quantified at 72 h after RNA transfection using an MTT Cell Proliferation Assay Kit (Cayman Chemicals, Ann Arbor, Mich.), according to the manufacturer's instructions. The percent growth inhibition was calculated by using the following equation: % growth inhibition=$([O.D.]_{untreated}-[O.D.]_{treated})/[O.D.]_{untreated}\times 100$. The induction of cell death was measured 48 h after RNA transfection by flow cytometry after staining with Annexin V-PE and 7-Aminoactinomycin D (7-AAD) using the PE Annexin V Apoptosis Detection Kit I (BD Biosciences, San Jose, Calif.) and analyzed using the CellQuest software (BD Biosciences).

Immunoblot Analysis and Antibodies

Cell lysates were prepared in 1×RIPA buffer (Sigma) in the presence of the complete protease inhibitor cocktail (Roche). Twelve to 20 μg of protein lysates were electrophoretically separated on 4-20% Mini-PROTEAN® TGX™ polyacrylamide gels (Bio-Rad, Hercules, Calif.) and transferred to polyvinylidene fluoride (PVDF) membranes (Poly-Screen®, PerkinElmer). After rinsing in $TBST_{20}$, membranes were blocked for 1 h in 10% dry milk in $TBTS_{20}$, followed by overnight incubation with primary antibodies anti-MAVS (1:200) (E-3; Santa Cruz), anti-RIG-I (1:500) (D14G6; Cell Signaling, Danvers, Mass.), anti-MDA5 (1:500) (D74E4; Cell Signaling), anti-PKR (1:350) (Catalog No 3072; Cell Signaling), anti-cleaved caspase-9 (1:500) (D2D4; Cell Signaling), anti-cleaved caspase-7 (1:1,000) (D6H1; Cell Signaling), and anti-cleaved PARP (1:1,000) (D64E10; Cell Signaling). When different proteins were sequentially detected on the same membrane, membranes were treated for 8 minutes with Restore Western Blot Stripping Buffer (Thermo Scientific), washed, blocked and probed again, as described above. Primary antibodies were detected using horseradish peroxidase (HRP)-conjugated anti-rabbit (1:4,000) (NA934; GE Healthcare, Pittsburgh, Pa.) or anti-mouse (1:4,000) (NA931; GE Healthcare) secondary antibodies. Anti-β-tubulin-HRP (1:2,000) (9F3; Cell Signaling) and anti-β-actin (1:2000) (13E5; Cell Signaling) were used as loading controls. HRP activity was visualized using the Immun-Star™ WesternC™ Chemiluminescence Kit (Bio-Rad). In order to determine caspase activation and PRR expression, cell lysates were harvested at 24 h after RNA transfection. In order to confirm siRNA-mediated knockdown of MAVS and PRRs, cell lysates were harvested 6 days after the first transfection of siRNA.

Enzyme-Linked Immunosorbent Assay (ELISA)

Cells were transfected with RNAs as described above. At 24 hours after RNA transfection, culture supernatants were collected and stored at −80° C. for later analyses. The production of human IL-8 was analyzed with a human IL-8 ELISA kit (eBioscience). IFN-0 production was determined with a human IFN-β ELISA kit (PBL Biomedical Laboratories, Piscataway, N.J.) by following the manufacturer's instructions.

Statistical Analysis

Two-tailed, paired Student's t test was applied for determining statistical significance. Confidence intervals equal to or less than 0.05 constitute statistical significance.

RESULTS

Figure 1B:
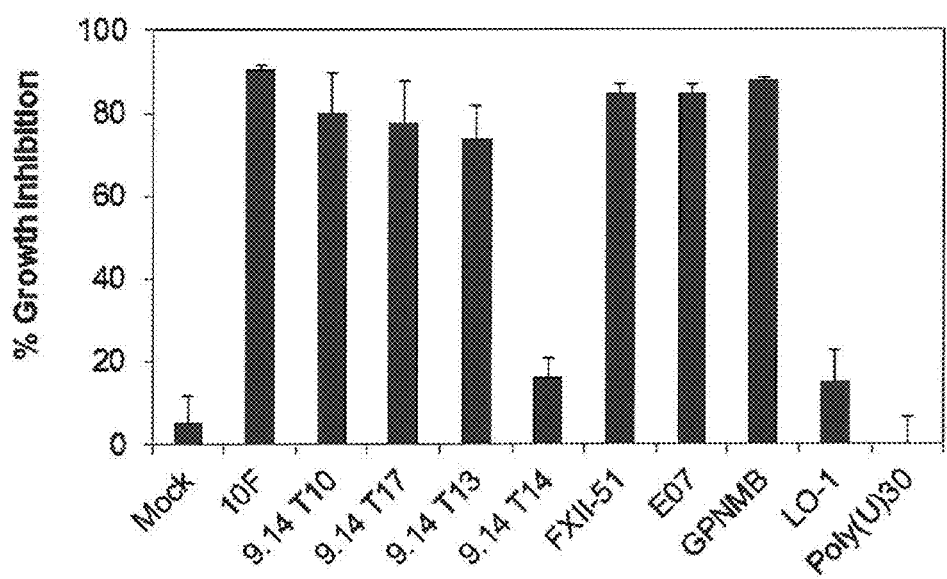
FIG. 1B is a graph showing the percent growth inhibition of a cell line after transfection with the indicated aptamer. Human melanoma cell line, WM266-4 cells were either treated with transfection reagent alone (mock) or transfected with 0.5 µg/ml of RNA aptamers 10F (SEQ ID NO: 4), vWF9.14T10 (SEQ ID NO: 6), vWF9.14T17 (SEQ ID NO: 7), vWF9.14T13 (SEQ ID NO: 9), vWF9.14T14 (SEQ ID NO: 8), FXII-51 (SEQ ID NO: 10), EGFR-E07 (SEQ ID NO: 11) or GPNMB (SEQ ID NO: 5). LO-1 is represented by SEQ ID NO: 12 and Poly(U)30 is represented by SEQ ID NO: 13. All RNAs contain 5'ppp and 2'F pyrimidine. The growth inhibition was measured by an MTT assay.

Intracytoplasmic Delivery of 5'ppp-2'F RNA Aptamers Inhibits Melanoma Cell Growth and Induces Programmed Cell Death in a Sequence-Independent and Structure-Dependent Manner Short, structured 5'ppp ssRNAs can be recognized by various RNA-sensing PRRs including RIG-I, PKR and TLR7 and induce type I IFN production by multiple human cells (Diebold et al. (2004) Science 303: 1529-1531; Heil et al. (2004) Science 303: 1526-1529; Besch et al. (2009) J Clin Invest 119: 2399-2411; Toroney et al. (2012) RNA 18: 1862-1874; and Schmidt et al. (2009) Proc Natl Acad Sci USA 106: 12067-12072). Interestingly, introduction of these 5'ppp ssRNAs into the cytoplasm could selectively kill human melanoma cells in a RIG-I-dependent and IFN-independent manner (Besch et al. (2009) J Clin Invest 119: 2399-2411). RNA aptamers are short ssRNAs (30-100 bases) that are often designed to bind to proteins. Most of the in vitro transcribed (IVT) RNA aptamers contain 2' ribose modifications, 5'ppp and a high degree of secondary structure, similar to PRR-activating ssRNAs except with nucleotide modifications. To test whether IVT RNA aptamers have anti-melanoma activity, we generated diverse RNA aptamers bearing 5'ppp and 2'F pyrimidines that can recognize different protein receptors (FIG. 1, Table 1). Surprisingly, all IVT RNA aptamers except short RNA aptamer 9.14 T14 tested in this study readily induced more than 80% growth inhibition of human melanoma cells within 72 hours after liposomal transfection, at least in part by the induction of apoptosis (FIG. 1B and FIG. 2A). Because this anti-melanoma effect was also seen with the various IVT RNA aptamers, but not with 5'ppp-2'F ssRNAs predicted to have minimal secondary structures, such as Poly(U)30 and LO-1, we concluded that the induction of anti-melanoma responses by 5'ppp-2'F RNA aptamers is largely dependent on the presence of folded secondary structure(s) rather than sequence.

Transfection with 5'ppp-2'F RNA Aptamers can Induce Caspase-Mediated Programmed Cell Death and Innate Immune Activation of Human Melanoma Cells 5'ppp-2'F RNA aptamer-induced apoptosis is accompanied by the activation of caspase-9, an initiator caspase of the intrinsic apoptosis pathway and its downstream effector molecules, including caspase-7 and poly(ADP-ribose) polymerase (PARP) (FIG. 2B). Certain cationic liposomes used as non-viral vectors have been shown to induce apoptosis (Iwaoka et al. (2006) J Leukoc Biol 79: 184-191). RNA aptamer-mediated cell death, however, is not dependent on non-specific cytotoxicity associated with liposomal transfection because direct intra-cytoplasmic delivery of RNA aptamers by electroporation also inhibited melanoma cell growth (FIG. 2C). 5-Fluorouracil (5-FU) is a pyrimidine analog and broadly used as an anti-metabolic agent that induces apoptosis by inhibiting DNA and RNA synthesis (Longley et al. (2003) Nat Rev Cancer 3: 330-338). One can argue that, unlike PRR-activating 5'ppp ssRNAs, RNA aptamers containing 2'F pyrimidines may interfere with DNA and RNA synthesis within melanoma cells, resulting in non-specific inhibition of melanoma cell proliferation. To test this possibility, human melanoma cells were electroporated with the 5'ppp-2'F RNA aptamer, 2'F pyrimidine ribonucleoside triphosphate (2'F NTP) or PBS. The electroporation of RNA aptamers induced apoptosis of melanoma cells as efficiently as the liposomal transfection of these RNAs, however, the 2'F NTP transfection did not alter melanoma cell viability (FIG. 2C). Moreover, transfection of 5'ppp-2'F RNA aptamers led to a strong induction of innate immune RNA-sensing PRRs, including RIG-I, MDA-5, and PKR, which was not observed upon treatment of the cells with staurosporine, a conventional apoptosis-inducing drug (FIG. 2D). These data suggest that the 5'ppp-2'F RNA aptamer employs a unique mechanism to induce melanoma growth inhibition, apoptosis and innate immune activation as compared to a conventional pro-apoptotic agent.

The RIG-I-MAVS Signaling Pathway Regulates the Induction of Anti-Melanoma Responses by 5'ppp-2'F RNA Aptamers Foreign, non-self RNAs are recognized by multiple RNA-sensing PRRs, including endosomal TLR3 and TLR7 and cytoplasmic RIG-I, MDA-5 and PKR. Direct cytoplasmic delivery of 5'ppp-2'F RNA aptamers by electroporation results in similar growth inhibition of melanoma cells as compared to liposomal transfection (FIG. 2C). Furthermore, liposomal transfection of 5'ppp-2'F RNA aptamers did not activate human TLR3 and TLR7 (FIGS. 3A and 3B, respectively). These data suggest that 5'ppp-2'F RNA aptamers activate cytoplasmic RNA-sensing PRRs rather than endosomal TLRs to induce cell death of melanoma cells. To determine the cytoplasmic PRR responsible for the recognition of 5'ppp-2'F RNA aptamers, we transiently knocked-down the expression of cytoplasmic RNA-sensing PRRs, including RIG-I, MDA-5 and PKR and an essential mitochondrial adaptor for RIG-I and MDA-5 signaling-induced apoptosis, MAVS, using specific 5'OH siRNAs. Consecutive knockdown of PRRs and MAVS in WM266-4 cells sustained knockdown effect at the protein level until day 6 post-transfection (FIG. 4A), which provided sufficient time for studying the cytotoxic effect of 5'ppp-2'F RNA transfection. Depletion of either RIG-I or MAVS significantly rescued the cells from 5'ppp-2'F RNA-induced cytotoxicity (FIG. 4B) and reduced IFNβ production by human melanoma cells transfected with 5'ppp-2'F RNA aptamers (FIG. 4C). Thus, RIG-I and MAVS are required for the recognition of 5'ppp-2'F RNA aptamers and the downstream signal transduction, respectively, ultimately inducing cell death and IFN expression. In contrast, knockdown of MDA-5 had no effect on cell viability, whereas depletion of PKR may even enhance the cytotoxic effect of 5'ppp-2'F RNA aptamers. An essential component of substrates that are recognized by RIG-I is a 5'ppp. Dephosphorylation of 5'ppp-2'F RNA aptamers, 10F and 9.14T10, partially prevented apoptosis and IFNβ production by human melanoma cells but did not completely eliminate it, most likely because of inefficient dephosphorylation (FIGS. 4D and E). Therefore, we evaluated a chemically synthesized version of the 2'F 9.14T10 aptamer without 5'ppp (Syn9.14T10), and observed that this synthetic aptamer completely lacked cytotoxic and IFN induction activities. These observations further support the hypothesis that RIG-I is the prominent cytoplasmic PRR recognizing 5'ppp-2'F RNA aptamers.

IFNβ-Dependent and Independent Mechanisms of 5'ppp-2'F RNA-Induced Cell Death and Growth Inhibition of Human Melanoma Cells IFNβ is a pleiotropic cytokine that can inhibit proliferation and induce cell death (Trinchieri (2010) J Exp Med 207: 2053-2063). It has a wide range of immune stimulatory activities including augmentation of T helper type 1 (Th1) cell responses, upregulation of MHC class I molecules, generation of natural killer (NK) cell- and T cell-mediated cytotoxicity and anti-tumor activities including anti-proliferative, anti-angiogenic and pro-apoptotic effects (Trinchieri (2010) J Exp Med 207: 2053-2063). To determine the contribution of IFNβ to 5'ppp-2'F RNA-induced melanoma cell death, cells were co-treated with B18R, a vaccinia-virus-encoded decoy receptor for type I IFN to neutralize IFNβ in the media and to abrogate autocrine/paracrine IFN signaling. While co-treatment with BI 8R only partially rescued 5'ppp-2'F 10F-transfected melanoma cells from cell death, it completely abolished the apoptosis of melanoma cells treated with either recombinant IFNβ or culture supernatants isolated from melanoma cells transfected with 5'ppp- 2'F 10F (FIG. 5A). The IFNβ-containing culture supernatants isolated from 5'ppp-2'F 10F-transfected melanoma cells minimally affected the growth of normal non-melanocytic cells, such as human dermal fibroblasts (FIG. 5A). Our data suggest that transfection of 5'ppp-2'F RNAs can induce growth inhibition and apoptosis of human melanoma cells through both type 1 IFN-dependent and -independent mechanisms, and autocrine/paracrine IFNβ can induce collateral growth inhibition of otherwise untreated melanoma cells.

Melanoma, Prostate Cancer and Glioblastoma Cells are Highly Sensitive to 5'ppp-2'F RNA-Induced Cytotoxicity when Compared to Other Types of Cells Next, we investigated whether 5'ppp-2'F RNA-induced cytotoxicity is specific for human melanoma cells. While 5'ppp-2'F RNAs inhibited the growth of human melanoma cell lines (WM266-4, WM115, SK-MEL2, and MALME-3M), human prostate cancer cell lines (PC-3, DU145 and LNCaP) and human glioblastoma cell lines (LN-229, Xeno-43 and A-172) no significant cytotoxic effects of 5'ppp-2'F RNAs were observed after transfection of other types of human cancer cells, including pancreatic cancer (Panc-1), cervical cancer (HeLa), breast cancer (Hs578T), fibrosarcoma (HT1080), ovarian cancer (SK-OV-3) and non-small cell lung cancer (NCI-H1838) (FIG. 5B). Furthermore. 5'ppp-2'F RNA transfection did not cause significant cytotoxic effects in a variety of human non-malignant cells including dermal fibroblasts, lung fibroblasts, colon epithelia cells, pancreatic ductal epithelial cells (HPDE), bone marrow stromal cells and PBMCs, whereas the growth of primary human melanocytes was inhibited by 5'ppp-2'F RNA aptamer transfection. This result suggests that melanocytic cells and prostate cancer cells are much more sensitive to 5'ppp-2'F RNA-induced cytotoxicity as compared to other types of cells.

The 2'F Modification Increases Anti-Cancer Activity, Innate Immune Activation and Nuclease Resistance of RIG-I-Activating 5'ppp RNAs 2'OMe-modified RNAs have been widely described as being able to evade innate immune recognition by RNA-sensing PRRs (Robbins et al. (2007) Mol Ther 15: 1663-1669 and Sioud (2010) Methods Mol Biol 629: 387-394). However, the influence of 2'F modifications on PRR sensing is much less clear; indeed, examples of both reduced and enhanced innate immune recognition have been reported (Uzri and Gehrke (2009) J Virol 83: 4174-418; Nallagatla and Bevilacqua (2008) RNA 14: 1201-1213; Hwang et al. (2012) Nucleic Acids Res 40: 2724-2733). In order to better dissect the contribution of 2'-ribose modifications to 5'ppp-2'F RNA-induced cytotoxicity, we established 5'ppp 10F RNAs with 2'OMe pyrimidine, 2'F pyrimidine or unmodified pyrimidine (2'OH). Transfection of these 5'ppp RNA variants into melanoma cells revealed that substituting 2'OH with 2'OMe completely abolished the cytotoxicity and cytokine production, whereas 2'F-modified 5'ppp RNAs significantly increased the cytotoxicity and IFNβ and IL-8 production over 2-fold compared to unmodified 5'ppp RNAs (FIGS. 6A and B). Transfection of 5'ppp-2'F 10F RNAs into human melanoma cells led to strong induction of cytokine production and growth inhibition, comparable to levels observed for the gold standard PRR-activating anti-cancer agent, polyI:C. Finally, unmodified 5'ppp 10F RNAs instantly degraded after exposure to serum, whereas 2'F modifications could render the 5'ppp 10F RNAs resistant to serum degradation (FIG. 6C). Furthermore, 2'F modification improve cellular stability of 5'ppp ssRNAs compared to unmodified RNAs (FIG. 6D). Although 2'OMe modification could augment serum stability of 5'ppp RNAs, this RNA modification eliminated the anti-cancer activity and innate immune activation of 5'ppp RNAs. Unlike the 2'OMe modification, the 2'F modification not only enhanced serum stability but also cancer cell death and innate immune activation. Therefore, increasing nuclease resistance of RNAs by the 2'F modification cannot be the sole mechanism of action for the enhancement of anti-cancer and innate immune activation of modified 5'ppp RNAs.

The ability of a dsRNA to induce cell cytotoxicity was also tested. Melanoma cells were transfected with 5'ppp-2'F dsRNA or 5'ppp-2'OH dsRNA and induction of apoptosis determined by Annexin V staining of the cells. As shown in FIG. 7, 5'ppp-2'F short dsRNA induced Annexin V and is killing the cells via apoptosis as demonstrated by increased 7-amino actinomycin D staining as well. In contrast, the 5'ppp-2'OH short dsDNA was not inducing apoptosis in the transfected cells.

Distance Between 5'ppp and Stem Structure is Inversely Correlated with Induction of Growth Inhibition and IFN Expression by 5'ppp-2'F ssRNAs in Human Cancer Cells The structure of RIG-I bound to 5'ppp RNA ligands suggested that both the 5'ppp and dsRNA motif are required for the initial recognition of RNA ligands by RIG-I (Jiang et al. (2011) Nature 479: 423-427). Schmidt et al. demonstrated that the minimal requirements of RIG-I-activating 5'ppp-2'OH ssRNAs for IFN production by human monocytes were 5'ppp and a 5- to 10-base-pair stem structure (Schmidt et al. (2009) Proc Natl Acad Sci USA 106: 12067-12072). Therefore, we hypothesized that short 5'ppp-2'F ssRNAs containing a single stem structure would induce IFN expression and cytotoxic effects in human melanoma cells. To test this hypothesis, we generated three different types of 5'ppp-2'F ssRNAs shorter than 30 nucleotides and containing only a single predicted stem-loop structure, including 1) Motif 1: 29-mer ssRNA with a 5' overhang stem-loop structure derived from the first 29 nucleotides of 5'ppp-2'F 10F, 2) Motif 2: truncated variant of Motif 1 (23-mer) with a blunt-end stem-loop structure and 3) Motif 3: extended variant of Motif 2 (30-mer) with an extended 3' end to generate a 3' overhang stem-loop structure (FIG. 8A and Table 1). Motif 1 treatment resulted in significantly lower cytotoxicity (P=0.0392) and IFNβ induction (P=0.0172) in human melanoma cells compared to 10F treatment, while Motif 2 treatment had 1.5- to 3-fold greater cytotoxicity (P=0.0039) and 3- to 10-fold greater IFN induction (P=0.0329) in the cells compared to 10F (FIGS. 8B and C). The difference between the cytotoxicity and IFNβ induction of Motif 3 and 10F treatments was not statistically significant. These data suggest that the distance between the 5'ppp and the internal stem structure is inversely correlated with recognition of 5'ppp 2'F ssRNAs by RIG-I. To support this finding, we generated an extended variant of Motif 1 with a longer 5' overhang (Motif 1A; FIG. 8A). As expected, treatment with Motif 1A resulted in a significantly decreased cytotoxic effect (P:=0.0409) and IFNβ production (P=0.0415) in human melanoma cells compared to treatment with Motif 1. Therefore, we concluded that a short blunt-ended stem-loop ssRNA containing 5'ppp and 2'F is a particularly potent immunostimulatory and anti-melanoma therapeutic RNA.

We claim:

1. A composition capable of inducing programmed cell death and cytokine or chemokine production in cells comprising a 5' triphosphate, 2' fluoro-modified pyrimidine non-linear single stranded RNA at least 17 nucleotides long,
   wherein the RNA comprises, in order, a 5' tail, a first stem region, a second stem region, and a 3' tail forming the non-linear structure by the complete or partial hybridization of the first stem region with the second stem region by at least 3 base pairings,
   wherein each of the 5' tail and the 3' tail comprises between 0 to 10 nucleotides, and
   wherein each of the first stem region and the second stem region comprise between 3 and 25 nucleotides.

2. The composition of claim 1, wherein the RNA is 20 or more ncleotides long.

3. The composition of claim 1, wherein the RNA is no more than 200 nucleotides long.

4. The composition of claim 1, wherein the 2' fluoro-modified pyrimidine includes at least one 2' fluoro-modified uridine.

5. The composition of claim 1, wherein at least 10% of the nucleotides contain a 2' fluoro-modification.

6. The composition of claim 5, wherein all of the pyrimidines are 2' fluoro-modified.

7. The composition of claim 5, wherein all of the uridine nucleotides are 2' fluoro-modified.

8. The composition of claim 5, wherein 50% of the nucleotides are 2'fluoro-modified.

9. The composition of claim 1, further comprising a cytoplasmic delivery composition.

10. The composition of claim 9, wherein the cytoplasmic delivery composition is selected from the group consisting of a liposome, synthetic polymer, cell-penetrating peptide, nanoparticle, viral particle, electroporation buffer and nucleofection reagent.

11. A method of inhibiting growth of cells or inducing cell death comprising contacting the cells with a composition comprising a 5' triphosphate, 2' fluoro-modified pyrimidine non-linear single stranded RNA at least 17 nucleotides long in an amount effective to inhibit cell growth, induce cell death or induce cytokine production, wherein the RNA comprise, in order, a 5' tail, a first stem region, a second stem region, and a 3' tail forming the non-linear structure by the complete or partial hybridization of the first stem region with the second stem region by at least 3 base pairings, wherein each of the 5' tail and the 3' tail comprises between 0 to 10 nucleotides, and wherein each of the first stem region and the second stem region comprise between 3 and 25 nucleotides.

12. A method of inhibiting growth of cells or inducing cell death comprising administering a composition comprising a 5' triphosphate, 2' fluoro-modified pyrimidine non-linear single stranded RNA at least 17 nucleotides long to a subject in need of such treatment in an amount effective to inhibit cell growth, induce cell death or induce cytokine production, wherein the RNA comprise, in order, a 5' tail, a first stem region, a second stem region, and a 3' tail forming the non-linear structure by the complete or partial hybridization of the first stem region with the second stem region by at least 3 base pairings, wherein each of the 5' tail and the 3' tail comprises between 0 to 10 nucleotides, and wherein each of the first stem region and the second stem region comprise between 3 and 25 nucleotides.

13. The method of claim 12, wherein the inhibition of growth or induction of cell death is independent of the RNA nucleotide sequence.

14. The method of claim 12, wherein the cells are selected from the group consisting of melanoma, brain cancer, prostate cancer, breast cancer, renal cancer, lung cancer, liver cancer, colorectal cancer, leukemia, lymphoma and ovarian cancer cells.

15. The method of claim 12, wherein the cells are infected with a virus.

16. The method of claim 12, further comprising administering an antigen.

17. The method of claim 12, wherein administration to the subject results in activation of pattern recognition receptors.

18. The method of claim 12, wherein the composition is delivered to the cytoplasm of cells.

19. The method of claim 18, wherein delivery to the cytoplasm is via a liposome, synthetic polymer, cell-penetrating peptide, nanoparticle or gene gun.

20. The method of claim 12, wherein the composition is delivered to the cells via receptor-mediated endocytosis.

21. The composition of claim 1, wherein the nonlinear structure is a hairpin structure and wherein the RNA further comprises a loop distal to the 5' triphosphate between the first stem region and the second stem region.

22. The composition of claim 1, wherein the RNA comprises a nucleotide sequence having 95% sequence identity to SEQ ID NO: 16.

* * * * *